(12) United States Patent
Svendsen et al.

(10) Patent No.: US 11,414,648 B2
(45) Date of Patent: Aug. 16, 2022

(54) METHODS AND COMPOSITIONS FOR PRODUCTION OF FALLOPIAN TUBE EPITHELIUM

(71) Applicant: CEDARS-SINAI MEDICAL CENTER, Los Angeles, CA (US)

(72) Inventors: Clive N. Svendsen, Pacific Palisades, CA (US); Beth Y. Karlan, Los Angeles, CA (US); Nur Yucer, Los Angeles, CA (US); Marie Holzapfel, Los Angeles, CA (US); Tilly Jenkins Vogel, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 344 days.

(21) Appl. No.: 16/496,062

(22) PCT Filed: Mar. 23, 2018

(86) PCT No.: PCT/US2018/024198
§ 371 (c)(1),
(2) Date: Sep. 20, 2019

(87) PCT Pub. No.: WO2018/176001
PCT Pub. Date: Sep. 27, 2018

(65) Prior Publication Data
US 2020/0032215 A1    Jan. 30, 2020

Related U.S. Application Data

(60) Provisional application No. 62/476,416, filed on Mar. 24, 2017.

(51) Int. Cl.
*C12N 5/071* (2010.01)
*A61K 35/48* (2015.01)

(52) U.S. Cl.
CPC ............ *C12N 5/0682* (2013.01); *A61K 35/48* (2013.01); *C12N 2501/155* (2013.01);
(Continued)

(58) Field of Classification Search
CPC .............. C12N 5/0682; C12N 2501/16; C12N 2501/392; C12N 2501/415; C12N 2501/999; C12N 2506/45
See application file for complete search history.

(56) References Cited

U.S. PATENT DOCUMENTS 6,300,080 B1    10/2001    Brenner et al.
7,989,197 B2    8/2011    Yoo et al.
(Continued)

FOREIGN PATENT DOCUMENTS

AU    2015204375 A1    8/2015
AU    2016341880 A1    5/2018
(Continued)

OTHER PUBLICATIONS

Kessler et al., The Notch and Wnt pathways regulate sternness and differentiation in human fallopian tube organoids. Nature Communications, vol. 6 (2015) 8989. (Year: 2015).*
(Continued)

*Primary Examiner* — Kara D Johnson
(74) *Attorney, Agent, or Firm* — Nixon Peabody LLP

(57) ABSTRACT

The fallopian tube epithelium (FTE) has been recognized as a site of origin of high-grade serous ovarian cancer (HGSC). However, absence of relevant in vitro human models that can recapitulate tissue-specific architecture has hindered understanding of FTE transformation and initiation of HGSC. Here, induced pluripotent stem cells (iPSCs) were used to establish a novel 3-dimensional (3D) human FTE organoid in vitro model containing the relevant cell types of the human fallopian tube as well as a luminal architecture (Continued)

that closely reflects the organization of fallopian tissues in vivo. Modulation of Wnt and nodal/activin signaling pathways provided iPSC differentiation into Müllerian cells and subsequent use of pro-Müllerian growth factors promoted FTE precursors. The expression of Müllerian markers verified correct cellular differentiation. An innovative 3D growth platform, which enabled the FTE organoid to self-organize into a convoluted luminal structure, permitted final differentiation to a FTE lineage. This powerful human-derived FTE organoid model can be used to study the earliest stages of HGSC development and to identify novel and specific biomarkers of early fallopian tube epithelial cell transformation.

19 Claims, 20 Drawing Sheets

Specification includes a Sequence Listing.

(52) U.S. Cl.
CPC .... *C12N 2501/16* (2013.01); *C12N 2501/392* (2013.01); *C12N 2501/415* (2013.01); *C12N 2501/999* (2013.01); *C12N 2506/45* (2013.01); *C12N 2513/00* (2013.01)

(56) References Cited

U.S. PATENT DOCUMENTS

| | | |
|---|---|---|
| 8,647,861 B2 | 2/2014 | Ingber et al. |
| 9,790,470 B2 | 10/2017 | Vallier et al. |
| 10,174,289 B2 | 1/2019 | Wells et al. |
| 2004/0247571 A1 | 12/2004 | Meijer et al. |
| 2007/0077649 A1 | 4/2007 | Sammak et al. |
| 2007/0128722 A1 | 6/2007 | Lin et al. |
| 2007/0281353 A1 | 12/2007 | Vacanti et al. |
| 2008/0044847 A1 | 2/2008 | Shusta et al. |
| 2008/0132445 A1 | 6/2008 | Ormandy et al. |
| 2008/0305086 A1 | 12/2008 | Poole |
| 2009/0075374 A1 | 3/2009 | Palecek et al. |
| 2009/0123383 A1 | 5/2009 | Frangioni |
| 2009/0258337 A1 | 10/2009 | Yagi |
| 2009/0317852 A1 | 12/2009 | Parker et al. |
| 2009/0324559 A1 | 12/2009 | Sakurada et al. |
| 2011/0097796 A1 | 4/2011 | Loa |
| 2011/0111499 A1 | 5/2011 | Torihashi |
| 2011/0245307 A1 | 10/2011 | Alkon |
| 2012/0094381 A1 | 4/2012 | Chambers et al. |
| 2012/0107934 A1 | 5/2012 | Poole |
| 2012/0128655 A1 | 5/2012 | Kim et al. |
| 2012/0171354 A1 | 7/2012 | O'Neill et al. |
| 2012/0211373 A1 | 8/2012 | El-Sayed et al. |
| 2013/0137130 A1 | 5/2013 | Wells et al. |
| 2013/0224857 A1 | 8/2013 | Blak et al. |
| 2013/0288969 A1 | 10/2013 | Scadden |
| 2014/0038279 A1 | 2/2014 | Ingber et al. |
| 2014/0065660 A1 | 3/2014 | Hanseup et al. |
| 2014/0093905 A1 | 4/2014 | Ingber et al. |
| 2014/0134732 A1 | 5/2014 | Ashton |
| 2014/0142370 A1 | 5/2014 | Wong et al. |
| 2014/0171380 A1 | 6/2014 | Kim et al. |
| 2014/0199700 A1 | 7/2014 | Kume et al. |
| 2014/0248621 A1 | 9/2014 | Collins |
| 2014/0288093 A1 | 9/2014 | Krainc et al. |
| 2014/0315990 A1 | 10/2014 | Alkon et al. |
| 2014/0329321 A1 | 11/2014 | Rajesh et al. |
| 2015/0017674 A1 | 1/2015 | Christensen et al. |
| 2015/0023928 A1 | 1/2015 | Hassiotou |
| 2015/0037320 A1 | 2/2015 | McGrath et al. |
| 2015/0151011 A1 | 6/2015 | Jang et al. |
| 2015/0218522 A1 | 8/2015 | Peterson et al. |
| 2015/0232810 A1 | 8/2015 | Luo et al. |
| 2015/0252328 A1 | 9/2015 | Woodruff et al. |
| 2015/0258124 A1 | 9/2015 | Katajisto et al. |
| 2015/0265652 A1 | 9/2015 | George et al. |
| 2015/0329828 A1 | 11/2015 | Rezania |
| 2016/0145642 A1 | 5/2016 | Cui et al. |
| 2016/0152950 A1 | 6/2016 | Zhang et al. |
| 2017/0107498 A1 | 4/2017 | Sareen et al. |
| 2017/0226478 A1 | 8/2017 | Kerns et al. |
| 2017/0240866 A1 | 8/2017 | Wells et al. |
| 2017/0253856 A1 | 9/2017 | Douvaras et al. |
| 2017/0283772 A1 | 10/2017 | Qian et al. |
| 2017/0292116 A1 | 10/2017 | Erlls et al. |
| 2017/0313976 A1 | 11/2017 | Kuwahara et al. |
| 2018/0021383 A1 | 1/2018 | George et al. |
| 2018/0057788 A1 | 3/2018 | Kerns et al. |
| 2018/0237741 A1 | 8/2018 | Gazit et al. |
| 2018/0298331 A1 | 10/2018 | Kerns et al. |
| 2018/0298332 A1 | 10/2018 | Kerns et al. |
| 2018/0305651 A1 | 10/2018 | Kerns et al. |
| 2018/0305668 A1 | 10/2018 | Gazit et al. |
| 2019/0009270 A1 | 1/2019 | Gazit et al. |
| 2019/0018000 A1 | 1/2019 | Gazit et al. |
| 2019/0031992 A1 | 1/2019 | Kerns et al. |
| 2019/0153395 A1 | 5/2019 | Barrett et al. |
| 2019/0194606 A1 | 6/2019 | Vatine et al. |
| 2019/0359924 A1 | 11/2019 | Kerns et al. |
| 2020/0000267 A1 | 1/2020 | Zuidervaart et al. |
| 2020/0071673 A1 | 3/2020 | Sareen et al. |
| 2020/0157508 A1 | 5/2020 | Barrett et al. |
| 2021/0000880 A1 | 1/2021 | Svendsen et al. |
| 2021/0023039 A1 | 1/2021 | Laperle et al. |
| 2021/0024886 A1 | 1/2021 | Laperle et al. |
| 2021/0033628 A1 | 2/2021 | Laperle et al. |
| 2021/0130774 A1 | 5/2021 | Sances et al. |

FOREIGN PATENT DOCUMENTS

| | | |
|---|---|---|
| AU | 2017213795 A1 | 8/2018 |
| AU | 2017214468 A1 | 9/2018 |
| AU | 2017319168 A1 | 3/2019 |
| AU | 2017321489 A1 | 3/2019 |
| AU | 2018235950 A1 | 10/2019 |
| AU | 2018236273 A1 | 10/2019 |
| AU | 2018270270 A1 | 12/2019 |
| AU | 2017319168 B2 | 4/2021 |
| AU | 2016341880 B2 | 5/2021 |
| CA | 3002399 A1 | 4/2017 |
| CA | 3013337 A1 | 8/2017 |
| CA | 3013357 A1 | 8/2017 |
| CA | 3034614 A1 | 3/2018 |
| CA | 3035058 A1 | 3/2018 |
| CA | 3055992 A1 | 9/2018 |
| CA | 3056089 A1 | 9/2018 |
| CA | 3064086 A1 | 11/2018 |
| EP | 3031908 A1 | 6/2016 |
| EP | 3365424 | 8/2018 |
| EP | 3411470 A2 | 12/2018 |
| EP | 3411472 A1 | 12/2018 |
| EP | 3503901 A1 | 7/2019 |
| EP | 3504319 A1 | 7/2019 |
| EP | 3768823 A1 | 1/2021 |
| EP | 3775161 A1 | 2/2021 |
| EP | 3787613 A1 | 3/2021 |
| EP | 3787649 A1 | 3/2021 |
| GB | 2561312 A | 10/2018 |
| GB | 2562406 A | 11/2018 |
| GB | 2564582 A | 1/2019 |
| GB | 2568446 A | 5/2019 |
| GB | 2569058 A | 6/2019 |
| GB | 2574988 A | 12/2019 |
| GB | 2575574 A | 1/2020 |
| GB | 2561312 B | 3/2021 |
| GB | 2564582 B | 9/2021 |
| HK | 1260726 B2 | 7/2021 |
| JP | 2014-171434 A | 9/2014 |
| JP | 2015-504676 A | 2/2015 |
| JP | 2018-533940 A | 11/2018 |
| JP | 2019-506861 A | 3/2019 |
| JP | 2021-520784 A | 8/2021 |
| JP | 2021-523700 A | 9/2021 |

(56) References Cited

FOREIGN PATENT DOCUMENTS

| | | |
|---|---|---|
| JP | 2021-523888 A | 9/2021 |
| KR | 20180069882 A | 6/2018 |
| SG | 11201803143Y A | 5/2018 |
| SG | 11201901621V A | 3/2019 |
| SG | 11201901628X A | 3/2019 |
| SG | 11201908358P A | 10/2019 |
| SG | 11201908359 U A | 10/2019 |
| WO | WO 2005/021720 A2 | 3/2005 |
| WO | WO 2010/009307 A2 | 1/2010 |
| WO | WO 2010/108005 A2 | 9/2010 |
| WO | WO 2011/109440 A1 | 9/2011 |
| WO | WO 2012/100084 A1 | 7/2012 |
| WO | WO 2012/118799 A2 | 9/2012 |
| WO | WO 2013/056216 A1 | 4/2013 |
| WO | WO 2013/065763 A1 | 5/2013 |
| WO | WO 2013/071282 A1 | 5/2013 |
| WO | WO 2013/086486 A1 | 6/2013 |
| WO | WO 2013/106677 A1 | 7/2013 |
| WO | WO 2013/184193 A2 | 12/2013 |
| WO | WO 2014/159356 A1 | 10/2014 |
| WO | WO 2014/172682 A1 | 10/2014 |
| WO | WO 2014/176606 A1 | 10/2014 |
| WO | WO 2015/052143 A1 | 4/2015 |
| WO | WO 2015/057261 A1 | 4/2015 |
| WO | WO 2015/126528 A1 | 8/2015 |
| WO | WO 2015/138032 A2 | 9/2015 |
| WO | WO 2015/138034 A2 | 9/2015 |
| WO | WO 2015/143342 A1 | 9/2015 |
| WO | WO 2015/153451 A1 | 10/2015 |
| WO | WO 2015/163823 A1 | 10/2015 |
| WO | WO 2015/181253 A1 | 12/2015 |
| WO | WO 2015/183920 A2 | 12/2015 |
| WO | WO 2015/188131 A1 | 12/2015 |
| WO | WO 2016/061464 A1 | 4/2016 |
| WO | WO 2016/063985 A1 | 4/2016 |
| WO | WO 2016/086040 A1 | 6/2016 |
| WO | WO 2016/093222 A1 | 6/2016 |
| WO | WO 2016/141137 A1 | 9/2016 |
| WO | WO 2016/162747 A1 | 10/2016 |
| WO | WO 2016/183252 A1 | 11/2016 |
| WO | WO 2017/035119 A1 | 3/2017 |
| WO | WO 2017/070224 A1 | 4/2017 |
| WO | WO 2017/075271 A1 | 5/2017 |
| WO | WO 2017/078807 A1 | 5/2017 |
| WO | WO 2017/123806 A1 | 7/2017 |
| WO | WO 2017/136462 A2 | 8/2017 |
| WO | WO 2017/136479 A1 | 8/2017 |
| WO | WO 2017/143049 A1 | 8/2017 |
| WO | WO 2017/200486 A1 | 11/2017 |
| WO | WO 2017/219000 A1 | 12/2017 |
| WO | WO 2018/044885 A1 | 3/2018 |
| WO | WO 2018/044934 A1 | 3/2018 |
| WO | WO 2018/140647 A1 | 8/2018 |
| WO | 2018/176001 A1 | 9/2018 |
| WO | WO 2018/170139 A1 | 9/2018 |
| WO | WO 2018/170180 A1 | 9/2018 |
| WO | WO 2018/213773 A1 | 11/2018 |
| WO | WO 2019/178550 A1 | 9/2019 |
| WO | WO 2019/183597 A1 | 9/2019 |
| WO | WO 2019/195798 A1 | 10/2019 |
| WO | WO 2019/195800 A1 | 10/2019 |
| WO | WO 2019/212690 A1 | 11/2019 |
| WO | WO 2019/212691 A1 | 11/2019 |
| WO | WO 2021/081229 A1 | 4/2021 |

OTHER PUBLICATIONS

Vogel et al., Co-culture of human induced pluripotent stem cells (iPSCs) with human fallopian tube epithelium (FTE) induces Pax8 and CK7 expression: Initial steps in modeling fallopian tube epithelium to study serous carcinogenesis. Gynecologic Oncology, vol. 137, No. 1 (2015) 206. (Year: 2015).*
ISR and WO for PCT/US2018/024198 dated Aug. 13, 2018, 15 pages.
Chen, et al., Chemically defined conditions for human iPSC derivation and culture, 2011, Nat. Methods, 8(5), 8 pages.
Araoka, et al., Efficient and rapid induction of human iPSCs/ESCs into nephrogenic intermediate mesoderm using small molecule-based differentiation methods, PLoS One, 2014, 9(1), 14 pages.
Rey, et al., Chapter 7, Sexual Differentiation, 2016 [online]. [Retrieved on Sep. 19, 2019]. Retrieved from the internet <URL:https://www.endotext.org/wp-content/uploads/pdfs/sexual-differentiation.pdf>, 106 pages.
Vogel, et al., Co-culture of human induced pluripotent stem cells 9iPSCs) with human fallopian tube epithelium (FTE) induces Pax8 and CK7 expression: Initial steps in modeling fallopian tube epithelium to study serous carcinogenesis; Gynecologic Oncology, 2015 137(1):206.
Levanon, et al., Primary ex vivo cultures of human fallopian tube epithelium as a model for serous ovarian carcinogenesis, Oncogene, 2010, 29(8):1103-1113.
International Search Report and Written Opinion of PCT/US2017/013250 dated Mar. 31, 2017, 12 Pages.
International Search Report and Written Opinion of PCT/US2016/057724 dated Jan. 9, 2017, 17 Pages.
International Search Report and Written Opinion of PCT/US2017/016098 dated Jun. 22, 2017, 14 Pages.
International Search Report and Written Opinion of PCT/US2017/016079 dated Jul. 25, 2017, 26 Pages.
International Search Report and Written Opinion of PCT/US2017/049193 dated Nov. 6, 2017, 9 Pages.
International Search Report and Written Opinion of PCT/US2017/049115 dated Nov. 28, 2017, 11 Pages.
International Search Report and Written Opinion of PCT/US2018/015318 dated May 2, 2018, 16 pages.
International Search Report and Written Opinion of PCT/US2018/022511 dated Jul. 26, 2018, 11 Pages.
International Search Report and Written Opinion of PCT/US2018/033498 dated Aug. 9, 2018, 9 Pages.
International Search Report and Written Opinion for PCT/US2018/022455 dated Aug. 23, 2018, 13 pages.
International Search Report and Written Opinion of PCT/US2019/026193 dated Jan. 7, 2019, 8 pages.
International Search Report and Written Opinion of PCT/US2019/026178 dated Jun. 11, 2019, 14 Pages.
International Search Report and Written Opinion of PCT/US2019/026183 dated Jun. 12, 2019, 10 Pages.
International Search Report and Written Opinion of PCT/US2019/026195 dated Jun. 12, 2019, 10 pages.
International Search Report and Written Opinion of PCT/US2019/023749 dated Jun. 25, 2019, 12 Pages.
International Search Report and Written Opinion for PCT/US2020/056896 dated Oct. 22, 2020, 11 pages.
International Preliminary Report on Patentability for PCT/US2016/057724 dated Apr. 24, 2018, 15 pages.
International Preliminary Report on Patentability for PCT/US2017/013250 dated Jul. 17, 2018, 7 pages.
International Preliminary Report on Patentability for PCT/US2017/016098 dated Aug. 7, 2018, 10 pages.
International Preliminary Report on Patentability for PCT/US2017/016079 dated Aug. 7, 2018, 21 pages.
International Preliminary Report on Patentability for PCT/US2018/022511, dated Sep. 17, 2019, 8 pages.
International Preliminary Report on Patentability for PCT/US2018/022455 dated Aug. 23, 2018, 9 pages.
International Preliminary Report on Patentability for PCT/US2018/033498 dated Nov. 19, 2019, 8 pages.
International Preliminary Report on Patentability for PCT/US2017/049193 dated Mar. 5, 2019, 8 pages.
International Preliminary Report on Patentability for PCT/US2017/049115 dated Mar. 5, 2019, 8 pages.
International Preliminary Report on Patentability for PCT/US2018/015318 dated Jul. 30, 2019, 12 pages.
AU 2016341880 Examination Report dated Jan. 15, 2020, 5 pages.
AU 2017214468 Examination Report dated Dec. 10, 2019, 5 pages.
CA 3034614 Examination Report dated Jul. 5, 2019, 5 pages.

(56) References Cited

OTHER PUBLICATIONS

EP 16858141.1 Extended Search Report dated Mar. 15, 2019, 10 pages.
EP 17748100.9 European Partial Supplementary Search Report dated Sep. 18, 2019, 15 pages.
EP 17748100.9 European Extended Search Report dated Dec. 20, 2019, 12 pages.
EP 17748084.5 European Extended Search Report dated Sep. 10, 2019.
EP 17847396.3 European Extended Search Report dated, Jan. 28, 2020, 11 pages.
EP17847365.8 European Extended Search Report dated Jan. 21, 2020, 11 pages.
EP 19782199.4 Partial Supplementary Search Report dated Nov. 30, 2021, 15 pages.
EP 19796470.3 European Extended Search Report dated Dec. 10, 2021, 11 pages.
EP 19771249.0 Partial Supplemental European Search Report dated Nov. 8, 2011, 15 pages.
EP 18802136.4 Examination Report dated Oct. 14, 2021, 8 pages.
EP 18802136.4 Extended European Search Report dated Jan. 22, 2021, 12 pages.
EP 19782199.4 Extended European Search Report dated Mar. 3, 2022, 12 pages.
GB1811716.8 Examination Report dated Feb. 12, 2020, 6 pages.
GB 1903007.1 Search Report dated Apr. 1, 2019, 8 pages.
GB 1903007.1 Search Report dated Jun. 24, 2020, 3 pages.
JP 2018-540028 Notice of Reasons for Rejection dated Mar. 1, 2021.
SG 11201803143Y Search Report dated Jul. 15, 2019, 3 pages.
SG 11201901628X Written Opinion dated Mar. 10, 2021, 9 pages.
Abbott et al., Structure and function of the blood-brain barrier, Neurobiology of Desease, 2010 27:13-25.
Abbott et al., Structure and function of the blood-brain barrier, Pharm Tox BBB: 1-3, Feb. 2010, Conf. Abstract.
Action Potential, Wikipedia, pp. 1-29 Downloaded on Apr. 28, 2019, https://en.wikipedia.org/wiki/Action_potential.
Adriani et al., Modeling the Blood-Brain Barrier in a 3D Triple Co-Culture Microfluidic System, 37th Annual International Conference of the IEEE Engineering in Medicine and Biology Society, IEEE, pp. 338-341.
Akhtar et al., Inducible Expression of GDNF in Transplanted iPSC-Derived Nueral Progenitor Cells, Stem Cell Reports, 2018, vol. 10, pp. 1696-1704.
Amoroso M. W. et al., Accelerated High-Yield Generation of Limb-Innervating Motor Neurons from Human Stem Cells. J Neurosci, Jan. 9, 2013, vol. 33, No. 2, pp. 574-586 pp. 575 and 578, Fig. 1 and 2.
Armstrong et al., Human Induced Pluripotent Stem Cell Lines Show Stress Defense Mechanisms and Mitochondrial Regulation Similar to Those of Human Embryonic Stem Cells, 2010, Stem Cells, vol. 28(4), pp. 661-673.
Bai et al., BMP-2, VEGF and bFGF Synergistically Promote the Osteogenic Differentiation of Rat Bone Marrow-Derived Mesenchymal Stem Cells, Biotechnol Lett, 2013, vol. 35, pp. 301-308.
Barrett et al., Reliable Generation of Induced Pluripotent Stem Cells from Human Pymphoblastoid Cell Lines, 2014, Stem Cells Translational Medicine, vol. 3, pp. 1429-1434.
Ben-Zvi et al., Modeling Human Nutrition Using Human Embryonic Stem Cells, Cell, 2015, vol. 161(1), pp. 12-17.
Bhatia et al., Microfluidic Organs-on-Chips, Nature Biotechnology, 2014, vol. 32(8), pp. 760-772.
Bohrnsen et al. Supportive angiogenic and osteogenic differentiation of mesenchymal stromal cells and endothelial cells in monolayer and co-cultures. International Journal of Oral Science (2016) 8, 223-230 (Year: 2016).
Booth, Ross Hunter, a Microfluidic in Vitro Model of the Blood-Brain Barrier, Dissertation, 2014, pp. 1-177.
Boyer et al., More than a Bystander: The Contributions of Intrinsic Skeletal Muscle Defects in Motor Neuron Diseases, 2013, Frontiers in Physiology, vol. 4, Article 356, pp. 1-12.
Brittan et al., The gastrointestial stem cell, Cell Prolif., 2004, vol. 37, pp. 35-53.
Brown et al., Recreating Blood-Brain Barrier Physiology and Structure on Chip: A Novel Neurovascular Microfluidic Bioreactor, 2015, Biomicrofluidics, vol. 9(5).
Burkhardt et al., A Cellular Model for Sporadic ALS using Patient-Derived Induced Pluripotent Stem Cells, Molecular and Cellular Neuroscience, 2013, vol. 56, pp. 355-364.
Cashman et al., Induced Pluripotent Stem Cells and Motor Neuron Disease: Toward an Era of Individualized Medicine, J. Neurosci, 2013, vol. 33, pp. 8587-8589.
Chal et al., Differentiation of Pluripotent Stem Cells to Muscle Fiber to Model Duchenne Muscular Dystrophy, 2015, Nature Biotechnology, vol. 33(9), pp. 962-969.
Chen et al., Surface Marker Epithelial Cell Adhesion Molecule and E-Cadherin Facilitate the Identification and Selection of Induced Pluripotent Stem Cells, 2011, Stem Cell Rev., vol. 7(3), pp. 722-735.
Chou et al., Efficient human iPS cell derivation by a non-integrating plasmid from blood cells with unique epigenetic and gene expression signatures, Cell Research, 2011, 21:3, pp. 518-529.
Danmark et al., Development of a novel microfluidic device for long-term in situ monitoring of live cells in 3-dimensional matrices, Biomed Microdevices, 2012, pp. 885-893.
Date et al., Mini-Gut Organoids: Reconstruction of the Stem Cell Niche, Annu. Rev. Cell Dev. Biol., 2015, vol. 31, pp. 269-289.
Demers et al., Development-on-Chip: in vitro Neutral Tube Patterning with a Microfluidic Device, Development, 2016, vol. 143(11), pp. 1884-1892.
Dhumpa et al., Temporal Gradients in Microfluidic Systems to Probe Cellular Dynamics: A Review, Anal. Chim. Acta, 2012, vol. 743, pp. 9-18.
Dimos et al., Induced Pluripotent Stem Cells Generated from Patients with ALS can be Differentiated into Motor Nuerons, Science, 2008, vol. 321, pp. 1218-1221.
Douville et al., Fabrication of Two-Layered Channel System with Embedded Electrodes to Measure Resistance Across Epithelial and Endothelial Barriers, 2010, Analytical Chemistry, vol. 82(6), pp. 2505-2511.
Ebert et al., EZ Spheres: A Stable and Expandable Culture System for the Generation of Pre-rosette Multipotent Stem Cells from Human ESCs and iPSCs., 2013, Stem Cell Research, vol. 10(3), pp. 417-427.
Esch et al., Organs-on-Chips at the Frontiers of Drig Discovery, Nature Reviews, 2015, vol. 14(4), pp. 248-269.
Evans et al., The Development of a Method for the Preparation of Rat Intestinal Epithelial Cell Primary Cultures, 1992, Journal of Cell Science, vol. 101, pp. 219-231.
Faravelli I. et al., Motor neuron derivation from human embryonic and induced pluripotent stem cells: Experimental approaches and clinical perspectives. Stem Cell Res Ther, Jul. 14, 2014, vol. 5, No. 4, pp. 87.
Farrelly et al., Extracellular matrix regulates apoptosis in mammary epithelium through a control on insulin signaling, The Journal of Cell Biology, 1999, 144(6):1337-1347.
Fridley et al., Hydrodynamic modulation of pluripotent stem cells, Stem cell research & therapy,2012, vol. 45.
Gao et al., Regulation of Cell Migration and Osteogenic Differentiation in Mesenchymal Stem Cells under Extremely Low Fluidic Shear Stress, Biomicrofluidics, 2014, vol. 8(5), Article No. 052008.
Gel, Wikipedia, pp. 1-29 Downloaded on Sep. 14, 2018, https://en.wikipedia.org/wiki/Gel.
Gracz et al., CD24 and CD44 Mark Human Intestinal Epithelial Cell Populations with Characteristics of Active and Facultative Stem Cells, 2013, Stem Cells, vol. 31(9), pp. 2024-2030.
Gross et al., Applications of Microfluidics for Neuronal Studies, 2007, Journal of the Neurological Sciences, vol. 252, pp. 135-143.
Gurusamy et al., Hepatocyte Growth Factor-Like Protein is a Positive Regulator of Early Mammary Gland Ductal Morphogenesis, Mechanisms of Development, 2014, vol. 133, pp. 11-22.

(56) References Cited

OTHER PUBLICATIONS

Hens et al., BMP4 and PTHrP interact to stimulate ductal outgrowth during embryonic mammary development and to inhibit hair follicle induction, Development, 2007, 134:1221-1230.

Hu et al. Neural differentiation of human induced pluripotent stem cells follows developmental principles but with variable potency, PNAS, 2010, vol. 107(9), pp. 4335-4340.

Hu et al., Derivation, Expansion and Motor Neuron Differentiation of Human-Induced Pluripotent Stem Cells with Non-Integrating Episomal Vectors and a Defined Xenogeneic-Free Culture System, Mol Neurobiol, 2016, vol. 53, pp. 1589-1600.

Hughes et al., Matrigel: A Complex Protein Mixture Required for Optimal Growth of Cell Culture, 2010, Proteomics, vol. 10, pp. 1886-1890.

Huh et al., From 3D Cell Culture to Organs-on-Chips, Trends in Cell Biology, 2011, vol. 21(2), pp. 745-754.

Huh et al., Microfabrication of Human Organs-on-Chips, Nature Protocols, 2013, vol. 8(11), pp. 2135-2157.

Hynds et al., Concise Review: The Relevance of Human Stem Cell-Derived Organoid Models for Epithelial Transitional Medicine, Stem Cells, 2013, vol. 131, pp. 417-422.

Jang et al., JAK-STAT Pathway and Myogenic Differentiation, JAKSTAT, 2013, vol. 2(2), pp. e23282-1 to e-23282-6.

Joo-Eun, L., Patient-Specific Induced Pluripotent Stem Cell Models of Variant Angina Derived from Peripheral Blood, The Department of Biomedical Sciences Seoul National University College of Medicine, Jul. 2017, pp. 1-75.

Jenke et al., DNA Methylation Analysis in the Intestinal Epithelium—Effect of Cell Separation on Gene Expression an Methylation Profile, PLOS One, 2013, vol. 8(2), pp. 1-8.

Jha et al., Motor Neuron differentiation from Pluripotent Stem Cells and Other Intermediate Proliferative Precursors that can be Discriminated by Lineage Specific Reports, Stem Cell Rev Rep, Aug. 2014, 11:194-204.

Kauffman et al., Alternative functional in vitro models of human intestinal epithelia, frontiers in Pharmacology, Jul. 2013, vol. 4, Article 79, 18 pages.

Kelamangalath et al. k-Opioid receptor inhibition of calcium oscillations in spinal cord neurons,, Molecular Pharmacology, 2011, 79:1061-1071.

Kilic et al., Brain-on-a-Chip Model Enables Analysis of Human Neuronal Differentiation and Chemotaxis, 2016, Lab on a Chip, vol. 16(21), pp. 4152-4162.

Kilpatrick, K. et al., Genetic and chemical activation of TFEB mediates clearance of aggregated a-synuclein, PLoS One, 2015, 10:3, pp. 1-21.

Kim et al. A practical guide to microfluidic perfusion culture of adherent mammalian cells. Lab Chip, 2007, 7, 681-694 (Year: 2007).

Kim et al., Human Gut-on-a-Chip Inhabited by a Microbial Flora that Experiences Intestinal Peristalsis-Like Motions and Flow, Lab on a Chip, 2012, vol. 12(12). pp. 2165.

Kim et al., Gut-on-a-Chip Microenvironmental Induces Human Intestinal Cells to Undergo Villus Differentiation, Integrative Biology, 2013, vol. 5(9), p. 1130-1140.

Kim et al. Shear Stress Induced by an Interstitial Level of Slow Flow Increases the Osteogenic Differentiation of Mesenchymal Stem Cells through TAZ Activation. PLoS One 9(3): e92427. p. 1-9 (Year: 2014).

Kim et al., Contributions of Microbiome and Mechanical Deformation to Intestinal Bacterial Overgrowth and Inflammation in a Human Gut-on-a-Chip, PNAS, 2015, vol. 113(1), pp. E7-E15.

Kirkby et al., A Role for Correlated Spontaneous Activity in the Assembly of Neural Circuits, 2013, Neuron, vol. 80(5), 27 Pages.

Kitamura et al., Possible Involvement of Both Mitochondria and Endoplasmic Reticulum-Dependent Caspase Pathways in Retenone-Induced Apoptosis in Human Neuroblastoma SH-SY5Y Cells, Neuroscience Letters, 2002, vol. 2002, pp. 25-28.

Kondo et al., Ipsc-based Coound screening and in vitro trials identify a synergistic anti-amyloid b combination for Alzheimer's Disease, Cell Reports, 2017, vol. 21, pp. 2304-2312.

Kreke et al. Effect of Intermittent Shear Stress on Mechanotransductive Signaling and Osteoblastic Differentiation of Bone Marrow Stromal Cells. Tissue Engineering: Part A vol. 14, No. 4, 2008. p. 529-537 (Year: 2008).

Kuratnik et al., Intestinal organoids at tissue surrogates for toxicological and pharmacological studies, biochemical Pharmacology, Apr. 25, 2013, vol. 85:12, pp. 1721-1726.

Kwasny et al., Static biofilm cultures of gram-positive pathogens grown in a microtiter format used for anti-biofilm drug discovery, Current Protocols in Pharmacology, 2010, 13A.8.1-13A.8.23.

Lee et al. Microfluidic 3D bone tissue model for high-throughput evaluation of would healing and infection-preventing biomaterials, Biomaterials 33.4 2012 999-1006.

Lenner, J., Fat Cells More Easily Programmed into iPS Cells, 2009, pp. 1-2.

Lenzi et al., Differentiation of Control and ALS Mutant Human iPSCs into Functional Skeletal Muscle Cells, A Tool for the Study of Neuromuscolar Diseases, Stem Cell Research, 2016, vol. 17, pp. 140-147.

Li et al., Protein kinase C controls lysosome biogenesis independently of mTORC1, Nature Cell Biology, 2016, 10:10, pp. 1-26.

Lin et al., Neural Stem Cell Differentiation in a Cell-Collagen-Bioreactor Culture System, 2004, Developmental Brain Research, vol. 153, pp. 163-173.

Lippmann, et al., Human Blood-Brain Barrier Endothelial Cells Derived from Pluripotent Stem Cells, 2012, Nature Biotechnology, vol. 30(8), pp. 783-791.

Lippmann et al., A Retinoic Acid-Enhanced, Multicellular Human Blood-Brain Barrier Model Derived from Stem Cell Sources, Scientific Reports, vol. 4(1), 2014, pp. 1-10.

Lippmann et al., Chemically Defined Differentiation of Human Pluripotent Stem Cells to Hindbrain and Spinal Cord Neural Stem Cells with Defined Regional Identifies, 2015, Protocol Exchange.

Loo et al., An Arduous Journey from Human Pluripotent Stem Cells to Functional Pancreatic Beta Cells, Diabetes Obes Metab., 2018, vol. 20(3), pp. 3-13.

Maegawa et al. Enhancement of osteoblastic differentiation of mesenchymal stromal cells cultured by selective combination of bone morphogenetic protein-2 (BMP-2) and fibroblast growth factor-2 (FGF-2). J Tissue Eng Regen Med 2007; 1: 306-313 (Year: 2007).

Martin et al., Laparoscopic Colorectal Resection in the Obese Patient, 2011, Clinics in Colon and Rectal Surgery, vol. 24(4), pp. 263-273.

Massumi et al., Efficient Programming of Human Eye Conjunctiva-Derived Induced Pluripotent Stem (ECiPS) Cells into Definitive Endoderm-Like Cells, Experimental Cell Research, 2014, vol. 322, pp. 51-61.

McGaugh et al., Efficient Differentiation of Pluripotent Stem Cells to NKX6-1 + Pancreating Progenitors, Journal of Visualized Experiments, 2017, vol. 121, pp. 1-5.

McKinney, C.E. et al., Using induced pluripotent stem cells derived neurons to model brain diseases, Neural Regeneration Research, 2017, 12:7 pp. 1-11.

Murphy et al., Scaffolds for 3D in vitro Culture of Neural Lineage Cells, Acta Biomaterialia, 2017, vol. 54, pp. 1-20.

Myotube, Medical Dictionary—Downloaded on Jul. 8, 2018, https://medical-dictionary.thefreedictionary.com/myotube, p. 1.

Naik et al., In vitro blood-brain models: Current and perspective technologies, J. Phar Sci., 2012, 1014(4):1337-1354.

Nicoleau et al., Embryonic Stem Cells Neural Differentiation Qualifies the Role of Wnt/[beta]-Catenin Signals in Human Telecephalic Specification and Regionalization. Human ESC Telencephalic Differentiation, Stem Cells, 2013, vol. 31(9), pp. 1763-1774.

Niego et al., Improved Method for the Preparation of a Human Cell-based, Contact Model of the Blood-Brain Barrier, 2013, J. Vis. Exp., vol. 81(e50934), pp. 1-9.

Nishimura et al. Effect of osteogenic differentiation medium on proliferation and differentiation of human mesenchymal stem cells

(56) References Cited

OTHER PUBLICATIONS in three dimensional culture with radial flow bioreactor. Regenerative Therapy 2 (2015) 24-31 (Year: 2015).
Nostro et al., Efficient Generation of NKX6-1+ Pancreatic Progenitors from Multiple Human Pluripotent Stem Cell Lines, Stem Cell Reports, 2015 4(4), pp. 591-604.
Ochetta et al., High-Throughput Microfluidic Platform for 3D Cultures of Mesenchymal Stem Cells, Towards Engineering Developmental Processes, Scientific Reports, 2015, vol. 5, Article No. 10288, pp. 1-12.
Okita et al., A More Efficient Method to Generate Integration-Free Human iPS Cells, 2011, Nature Methods, vol. 8(5), pp. 409-412.
Ong et al., A Gel-Free 3D Microfluidic Cell Culture System, Biomaterials, 2008, vol. 29, pp. 3237-3244.
Park et al., Chip-Based Comparison of the Osteogenesis of Human Bone Marrow and Adipose Tissue-Derived Mesenchymal Stem Cells under Mechanical Stimulation, PLOS One, 2012, vol. 7(9), pp. 1-12.
Perry et al., The Neuromuscular junction: Structure and function, downloaded from the internet (Neuromuscular junction: Parts, structure and steps/Kenhub>, pp. 1-6, downloaded Feb. 25, 2021.
Polini et al., Organs-on-a-Chip: A New Tool for Drug Discovery, Expert Opinion on Drug Discovery, 2014, vol. 9(4), pp. 335-352.
Polydimethylsiloxane—Wikipedia, dowloaded on Feb. 24, 2021 <Silicon dioxide—Wikipedia>, pp. 1-11.
Prabhakarpandian et al., SyM-BBB: A Microfluidic Blood Brain Barrier Model, Lab on a Chip, 2013, vol. 13(6), p. 1093.
Qian et al., A Simple and Efficient System for Regulating Gene Expression in Human Pluripotent Stem Cells and Derivatives, Stem Cells, 2014, vol. 32(5), pp. 1230-1238.
Qu et al., Differentiation of human induced pluripotent stem cells to mammary-like organoids, Stem Cell Reports, 2017, 8(2):205-215.
Rajesh et al., Human Lymphoblastoid B-Cell Lines Reprogrammed to EBV-Free Induced Pluripotent Stem Cells, 2011, Blood, vol. 118(7), pp. 1797-1800.
Rhee et al., Patterned Cell Culture Inside Microfluidic Devices, Lab Chip, 2005, vol. 5(1), pp. 102-107.
Roberts et al., Expression of the Thyroid Hormone Transports Monocarboxylate Transporter-8 (SLC16A2) and Organic Ion Transporter-14 (SLCO1C1) at the Blood-Brain Barrier, Endocrinol, 2008, vol. 149(12), pp. 6251-6261.
Rosenberg et al., Calcium Signaling in Neuronal Development, 2011, Cold Spring Harb Perspect Biol., vol. 3(a004259), 13 Pages.
Ryan et al., Progranulin is expressed within motor neurons and promotes neuronal cell survival, BMC Neuroscience, 2009, 10:130, pp. 1-22.
Sances et al., Modeling ALS with Motor Neurons Derived from Human Induced Pluripotent Stem Cells, Nature Neuroscience, 2016, vol. 19, pp. 542-553.
Santaguida et al., Side by Side Comparison Between Dynamic Versus Static Models of Blood-Brain-Barrier in vitro: A Permeability Study, Brain Research, 2006, vol. 1109(1), pp. 1-13.
Sareen et al., Human Neural Progenitor Cells Generated from Induced Pluripotent Stem Cells can Survive, Migrate, and Integrate in the Rodent Spinal Cord, Journal of Comparative Neurology, 2014, vol. 522(12), pp. 2707-2728.
Sareen et al., Targeting RNA foci in iPSC-Derived Motor Neurons from ALS Patients with C90RF72 Repeat Expansion, 2013, Science Translational Medicine, vol. 5(208), 208ra149, 26 Pages.
Schiesser et al., Derivation of Insulin-Producing Beta-Cells from Human Pluripotent Stem Cells, The Review of Diabetic Studies, 2014, vol. 11(1), pp. 6-18.
Schwartz et al., Allan-Herndon-Dudley Syndrome and the Monocalboxylate Transporter 8 (MCT8) Gene, 2005, AJHG, vol. 77(1), pp. 41-53.
Shimuzu et al., Microfluidic Devices for Construction of Contractile Skeletal Muscle Microtissues, J. Biosci. Bioeng., 2015, vol. 119, pp. 212-216.

Shimojo et al., Rapid, Efficient and Simple Motor Neuron Differentiation from Human Pluripotent Stem Cells, Molecular Brain, 2015, vol. 8(1), pp. 1-15.
Silicon dioxide—Wikipedia, downloaded on Feb. 24, 2021 <silicon dioxide—Wikipedia> pp. 1-20.
Simeone et al., The Otx Family, Pattern Formation and Development Mechanisms, 2002, vol. 12, pp. 409-415.
Soria-Valles et al., NF-kB Activation Impairs Somatic Cell Reprogramming in Ageing, 2015, Nat. Cell Biol., vol. 17(8), pp. 1004-1013.
Southam et al., Microfluidic primary culture model of the lower motor neuron-neuromuscular junction circuit, J Neurosc Meth 2013, 218:164-169.
Southam et al., A Novel in vitro Primary Culture Model of the Lower Motor Neuron Nueromuscular Junction Circuit, Microfludic and Compartmentalized Platforms for Neurobiological Research, Humana Press, 2015, pp. 181-193, abstract only.
Stepniewski et al., Induced Pluripotent Stem Cells as a Model for Diabetes Investigation, Scientific Reports, 2015, 5:8597, 14 pages.
Sundberg et al., Improved cell therapy protocol for Parkinson's Disease based on differentiation efficiency and safety of Hesc-, Hipsc and non-human primate Ipsc-derived DA neurons, Stem Cells, 2013, 31:8, pp. 1-25.
Sun et al., Role of Bone Morphogenetic Protein-2 in Osteogenic Differentiation of MesenChymal Stem Cells, Molecular Medicine Reports, 2015, vol. 12, pp. 4230-4237.
Telias et al., Electrical Maturation of Neurons Derived from Human Embryonic Stem Cells, F1000 Research, 2014, vol. 3(196), p. 1-12.
Tenstad et al., Extensive Adipogenic and Osteogenic Differentiation of Patterned Human Mesenchymal Stem Cells in a Microfluidic Device, Lab on a Chip, 2010, vol. 10(11), pp. 1401-1409.
Tian et al., Salvianolic Acid B, An Antioxidant from Saliva Miltiorrhiza, prevents 6-hydroxydopamine Induced Apoptosis in SH-SY5Y Cells, The International Science Journal of Biochemistry & Cell Biology, 2008, vol. 40, pp. 409-422.
Uzel et al., New Microfluidic Chip Replicates Muscle-Nerve Connection, 2016, Science Daily, pp. 1-4.
Uzel et al., Microfluidic Device for the Formation of Optically Excitable, Three-Dimensional, Compartmentalized Motor Units, Science Advances, 2016, pp. e1501429.
Vatine et al., Human iPSC-Derived Blood-Brain Barrier Chips Enable Disease Modeling and. Personalized Medicine Applications, Cell Stem Cell, 2019, vol. 24(6), pp. 995-1005.
Vatine et al., Human iPSC-Derived Blood-Brain Barrier Chips Enable Disease Modeling and Personalized Medicine Applications,Cell Stem Cell, 2019, vol. 24, Supplemental Figures, p. 1-10.
Wang et al., Microfluidics: A new cosset for neurobiology, Lab Chip, 2009, 9:644-652.
Wang et al., Androgen Receptor-Mediated Apoptosis in Bovine Testicular Induced Pluripotent Stem Cells in Response to Phthalate Esters, 2013, Cell Death Dis., vol. 4(e907), pp. 1-11.
Wang et al., Modeling the Mitochondrial Cardiomyopathy of Barth Syndrome with Induced Pluripotent Stem Cell and Heart-on-Chip Technologies, Nature Medicine, 2014, vol. 20(6), pp. 616-623.
Wang et al., Generation of an Induced Pluripotent Stem Cell Line (SHCDNi003-A) from a One-Year Old Chinese Han Infant with Allan-Herndon-Dudley Syndrome, Stem Cell Research, 2020, vol. 46, 4 pages.
Watson et al., Modelling the Endothelial Blood-CNS Barriers: A Method for the Production of Robust in Vitro Models of the Rat Blood-Brain Barrier and Blood-Spinal Cord Barrier, 2013, BMC Neuroscience, vol. 14(59), pp. 1-21.
Wehkamp et al., Reduced Paneth Cell [alpha]-Defensins in Ileal Crohn's Disease, PNAS, 2005, vol. 102, pp. 18129-18134.
Wu et al., Nuclear Accumulation of Histone Deacetylase 4 (HDAC4) Exerts Neurotoxicity in Models of Parkinson's Disease, Moi Neurobiol, 2017, vol. 54, pp. 6970-6983.
Workman et al., Intestine-Chip: A new model to understand the role of the Intestinal Epithelium in IBD by combining Microengineering Technology and IPSC-Derived human intestinal organoids, Gastroenterology, Apr. 1, 2017, vol. 152:5, Abstract only.
Workman et al., Enhanced Utilization of Induced Pluripotent Stem Cell-Derived Human Intestinal Organoids Using Microengineered

(56) References Cited

OTHER PUBLICATIONS

Chips, CMGH Cellular and Molecular Gastroenterology and Hepatology, 2018, vol. 5(4), pp. 669-677.
Yamamoto et al., Fluid Shear Stress Induces Differentiation of Flk-1-positive Embryonic Stem Cells into Vascular Endothelial Cells in vitro., 2004, Am. J. Physiol. Heart Circ. Physiol., vol. 288, pp. 1915-1924.
Yamamoto et al., The Stabilization Effect of Mesenchymal Stem Cells on the Formation of Microvascular Networks in a Microfluidic Device, Journal of Biomechanical Science and Engineering, 2013, vol. 8(2).
Yang et al., From the vascular microenvironment to neurogenesis, Brain Res Bull. Jan. 15, 2011; 84(1):1-7.
Yu et al., A Microfluidic-Based Multi-Shear Device for Investigating the Effects of Low Fluid-Induced Stresses on Osteoblasts, PLOS One, 2014, vol. 9(2), pp. 1-7.
Zhang et al., Regulation and Patterning of Cell Differentiation and Pluripotency, Thesis, Columbia University, pp. 1-177, 2011.
Zhang et al., FGF Ligands of the Postnatal Mammary Stroma Regulate Distinct Aspects of Epithelial Morphogenesis, Stem Cells and Regeneration, 2014, vol. 141, pp. 3352-3362.
Zhang et al., Patient-specific 3D microfluidic tissue model for multiple myeloma, Tissue Engineering Part C: Methods, 2014, pp. 663-670.
Zilio et al., Universal Hydrophilic Coating of Thermoplastic Polymers Currently Used in Microfluidics, 2014, Biomed. Microdevices, vol. 16(1), pp. 107-114.

\* cited by examiner

A a *MIXL1* b *BRACHYURY* a b

METHODS AND COMPOSITIONS FOR PRODUCTION OF FALLOPIAN TUBE EPITHELIUM

CROSS-REFERENCE TO RELATED APPLICATIONS

This application is the national phase of International Application No. PCT/US2018/024198, filed Mar. 23, 2018, which designated the U.S. and that International Application was published under PCT Article 21(2) in English. This application claims priority under 35 U.S.C. § 119(e) to U.S. Provisional Application No. 62/476,416, filed Mar. 24, 2017, the contents of which are herein incorporated by reference in their entirety.

FIELD OF THE INVENTION

Described herein are methods and compositions related to generation of fallopian tube cells and tissues from pluripotent stem cells.

BACKGROUND

High-grade serous carcinoma (HGSC), the most common subtype of epithelial ovarian cancer (~70%), has the highest mortality rate among all gynecological cancers. HGSC has a poor prognosis due to a combination of factors including late stage at diagnosis and a high predilection for developing drug resistance. It is now accepted that the majority of HGSCs arise from the secretory cells of the fallopian tube epithelium (FTE). The discovery of in situ lesions in the fallopian tube fimbriae, namely serous tubal intraepithelial carcinoma (STIC), supports the concept of the FTE origin of serous "ovarian" carcinoma. STICs are part of the high grade serous carcinogenic sequence and are believed to include early p53 mutations resulting in a "53 signature" that develops into invasive serous carcinoma of the fallopian tube, and that secondarily involves the nearby ovarian surface. The discovery of an extra-ovarian origin of ovarian cancer is a fundamental advance toward improving early detection, prevention and treatment of this lethal disease. However, the lack of relevant in vitro human models that can recapitulate tissue-specific architecture and study early alterations has hindered the further understanding of the mechanisms of FTE transformation as well as the initiation and progression of HGSC. Thus, there is a great need in the art for FTE cells, organoids and associated methods thereof.

Stem cell derived 3D organoid cancer models are emerging as powerful tools for understanding pathological processes at the molecular and cellular level, and they will be a critical platform to study the earliest stages of ovarian cancer development, which is poorly understood. By generating accurate organotypic human models of early-stage disease, the Inventors expect to be able to identify novel and specific biomarkers of early fallopian tube epithelial cell transformation. In the long term, this project could lead an identification of molecular targets for chemoprevention and thus significant reduction in the number of deaths from ovarian cancer each year.

Described herein is an iPSC-derived cellular model of fallopian tube epithelium development with numerous potential practical applications, including the identification of early biomarkers to stage disease progression and better classification of genetic risk factors. Methods and compositions for generating iPSC-derived FTE, including 3D organoids, offers a promising platform for validation of new drugs and targets, and modeling resistance to therapy within the tumor micro-environment in rapid, cost efficient manner. By generating iPSC-derived 3D FTE organoid model with various inherited mutant sample, one can elucidate specific mutant dependent response to treatment and can thereby predict the drug sensitivity of individual patients based on their unique spectrum of genetic mutations, allowing for guidance in treatment decisions and optimizing clinical outcomes in cancer patients.

SUMMARY OF THE INVENTION

Described herein is a method for generating a fallopian tube epithelium (FTE), including providing a quantity of human pluripotent stem cells (hPSCs), culturing the hPSCs in the presence of at least one first growth factor and at least one induction molecule to generate mesoderm cells, further culturing the mesoderm cells in the presence of at least one second growth factor, at least one second induction molecule, and at least first one kinase inhibitor to generate intermediate mesoderm (IM) cells, additionally culturing the IM cells in the presence of at least one third growth factor, and at least one second kinase inhibitor to generate Mullerian epithelium cells, and differentiating Mullerian epithelium cells by addition of at least one fourth growth factor into FTE. In other embodiments, the hPSCs are human induced pluripotent stem cells (hiPSCs). In other embodiments, the at least one first growth factor includes activin A, and the at least one induction molecule includes CHIR99021. In other embodiments, culturing the hPSCs includes about 2 days. In other embodiments, the at least one second growth factor includes BMP4, the at least one second induction molecule includes CHIR99021, and the at least one first kinase inhibitor includes ROCK inhibitor Y-27632. In other embodiments, further culturing the mesoderm cells includes about 2 days. In other embodiments, the at least one third growth factor includes WNT4 and at least one second kinase inhibitor includes ROCK inhibitor Y-27632. In other embodiments, additionally culturing the IM cells includes about 2 days. In other embodiments, the at least one fourth growth factor includes follistatin estrogen and progesterone. In other embodiments, the IM cells are organized as a spheroid. In other embodiments, spheroids are subsequently cultured in a matrix. In other embodiments, the FTE are organized as an organoid. In other embodiments, the FTE organoids are matured by further culturing for about 14-65 days. In other embodiments, mesoderm cells express one or more of: BRACHYURY and MIXL1. In other embodiments, IM cells express one or more of: PAX2, OSR1, GATA3, and WT1. In other embodiments, Mullerian epithelium cells express one or more of: WT1 and OVGP1. In other embodiments, Mullerian epithelium cells do not express one or more of: SIX2, FOXD1, CDX2 and NKX2-1.

Further described herein is a method of generating fallopian tube epithelium (FTE) organoids, providing a quantity of intermediate mesoderm (IM) cells, culturing the IM cells in a matrix and in the presence of at least one first growth factor, and at least first one kinase inhibitor to generate Mullerian epithelium cells, and differentiating Mullerian epithelium cells by addition of at least one second growth factor into FTE organoids. In other embodiments, the at least one first growth factor includes WNT4 and at least one kinase inhibitor includes ROCK inhibitor Y-27632. In other embodiments, culturing the IM cells includes about 2 days. In other embodiments, the at least one second growth factor includes follistatin estrogen and progesterone. In other embodiments, the FTE organoids are matured by further culturing for about 14-65 days. In other embodiments, the FTE organoids express one or more of: TUBB4A, FOXJ1, and PAX8.

Also described herein is a quantity of fallopian tube epithelium (FTE) organoids made by a method including generating fallopian tube epithelium (FTE) organoids, providing a quantity of intermediate mesoderm (IM) cells, culturing the IM cells in a matrix and in the presence of at least one first growth factor, and at least first one kinase inhibitor to generate Mullerian epithelium cells, and differentiating Mullerian epithelium cells by addition of at least one second growth factor into FTE organoids. In other embodiments, the at least one first growth factor includes WNT4 and at least one kinase inhibitor includes ROCK inhibitor Y-27632. In other embodiments, culturing the IM cells includes about 2 days. In other embodiments, the at least one second growth factor includes follistatin estrogen and progesterone. In other embodiments, the FTE organoids are matured by further culturing for about 14-65 days. In other embodiments, the FTE organoids express one or more of: TUBB4A, FOXJ1, and PAX8.

Further described herein is a composition of fallopian tube epithelium (FTE) organoids. Also described herein is a pharmaceutical composition, including a composition of FTE organoids and a pharmaceutically acceptable carrier.

DETAILED DESCRIPTION

Figure 1:
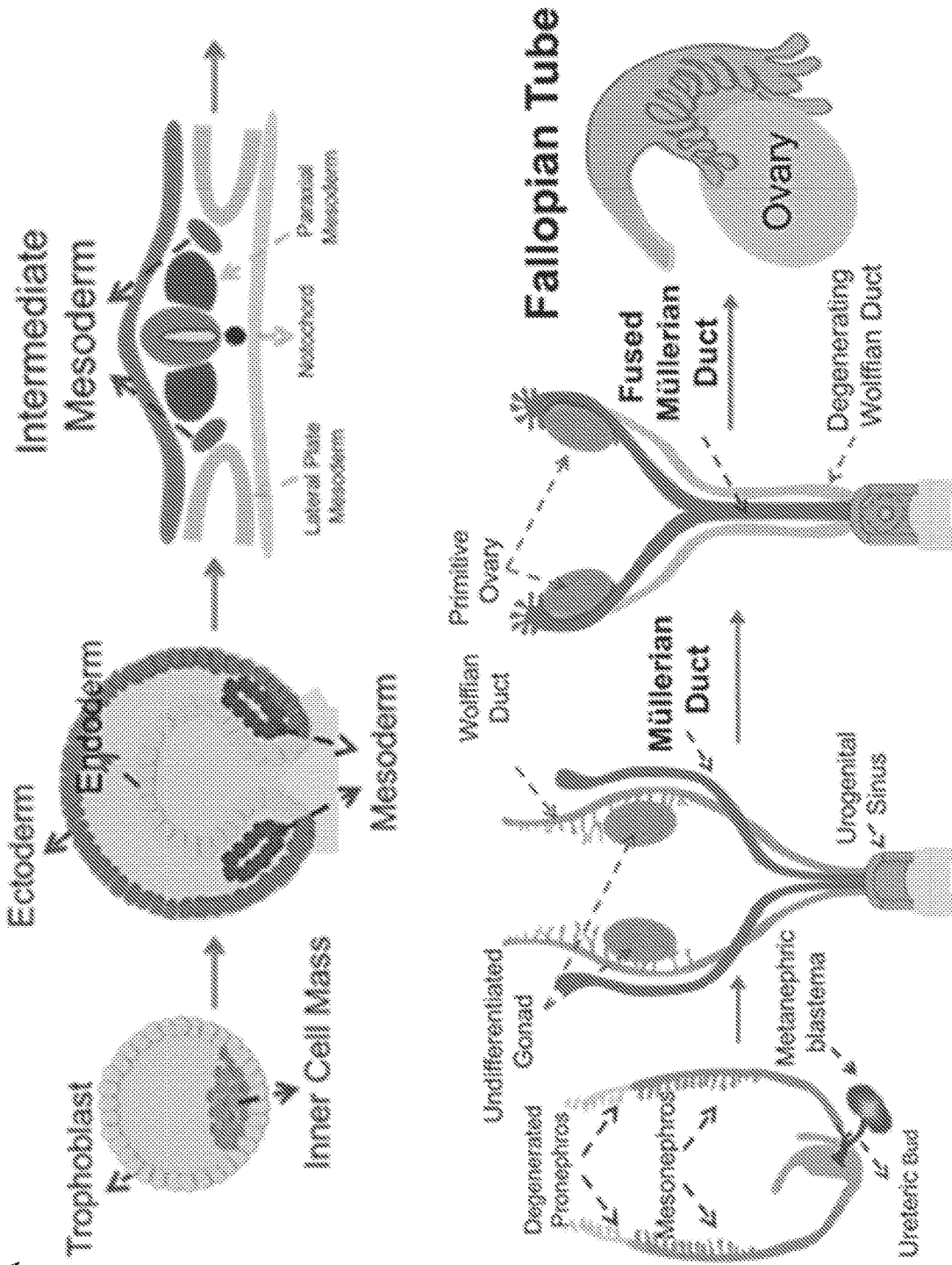
FIG. 1: Differentiation of Human iPSC into Intermediate Mesoderm-Like Cells. a) Schematic of developmental stages from inner cell mass to female reproductive tract and fallopian tube. b) Timeline and factors involved in the differentiation of iPSCs into intermediate mesoderm, c) Expression kinetics of mesoderm markers MIXL1- and BRACHYURY during the 6-day differentiation course using Mae et. al., protocol. Mae, S. et al. Monitoring and robust induction of nephrogenic intermediate mesoderm from human pluripotent stem cells. Nat Commun 4, 1367, doi:10.1038/ncomms2378 (2013). d) Immunocytochemistry demonstrating expression and localization of mesoderm marker BRACHYURY during differentiation. e) Expression of intermediate mesoderm markers, PAX2, OSR1, GATA3 and WT1 during the 6-day differentiation course. f) Pluripotency markers POU5F1, SOX2 and TDGF1 expression during the 6-day differentiation course. Relative gene expression to iPSC stage (Day 0) was calculated using □□Ct method and normalized endogenous GAPDH level for 87iCTR-n3 iPSC line. Error bars are Standard Error of the Mean (SEM) (n=3 independent experiments). ANOVA with Tukey post-hoc test was used for this analysis, with significance at $*p \leq 0.05$, $p \leq 0.01$, $**p \leq 0.0001$.
Figure 1:
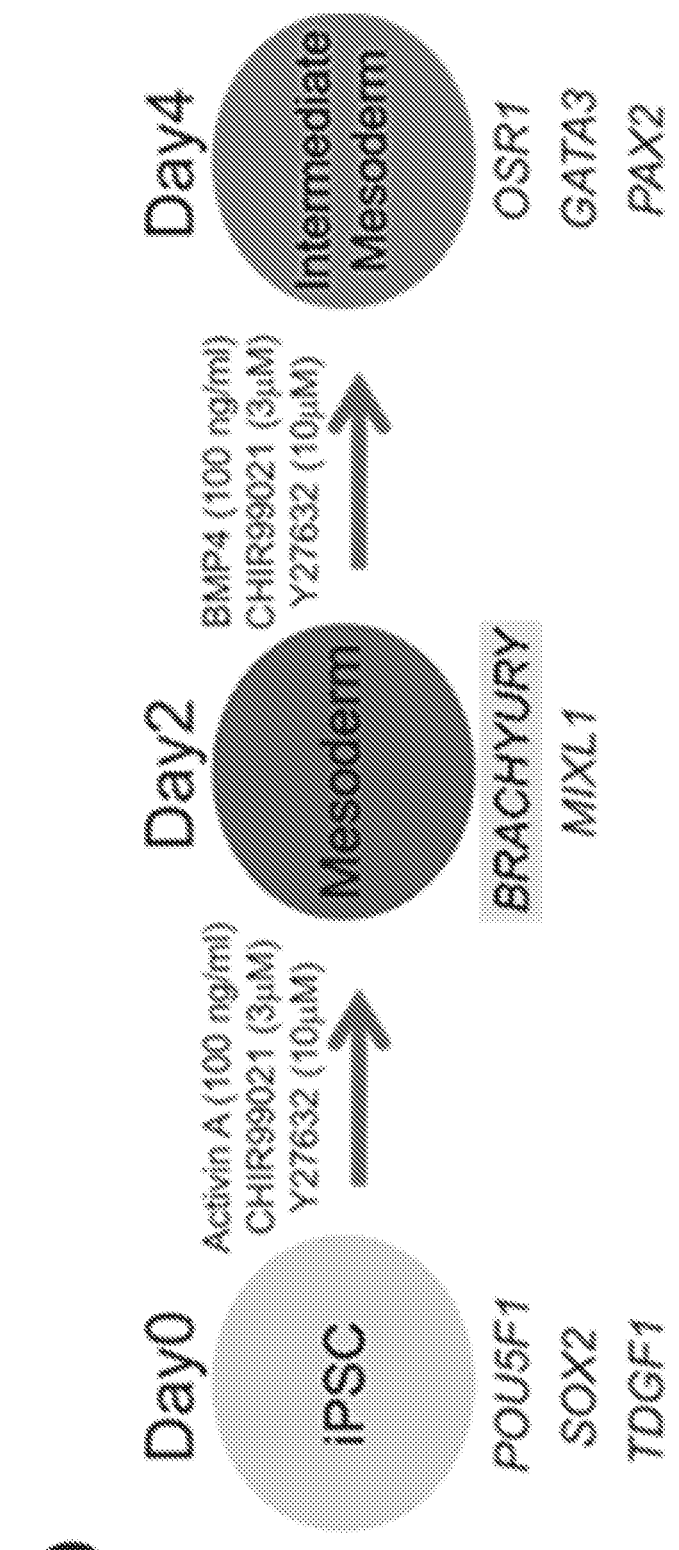
Figure 1:
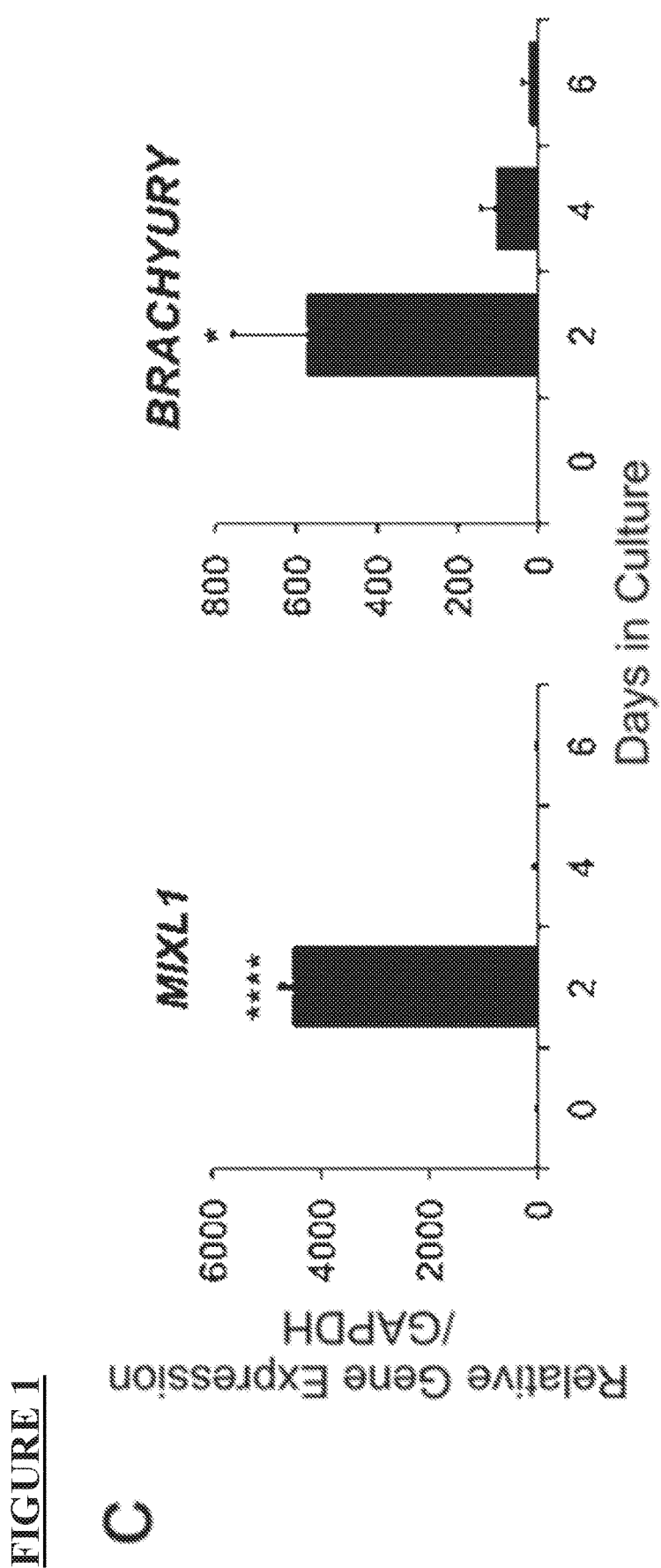
Figure 1:
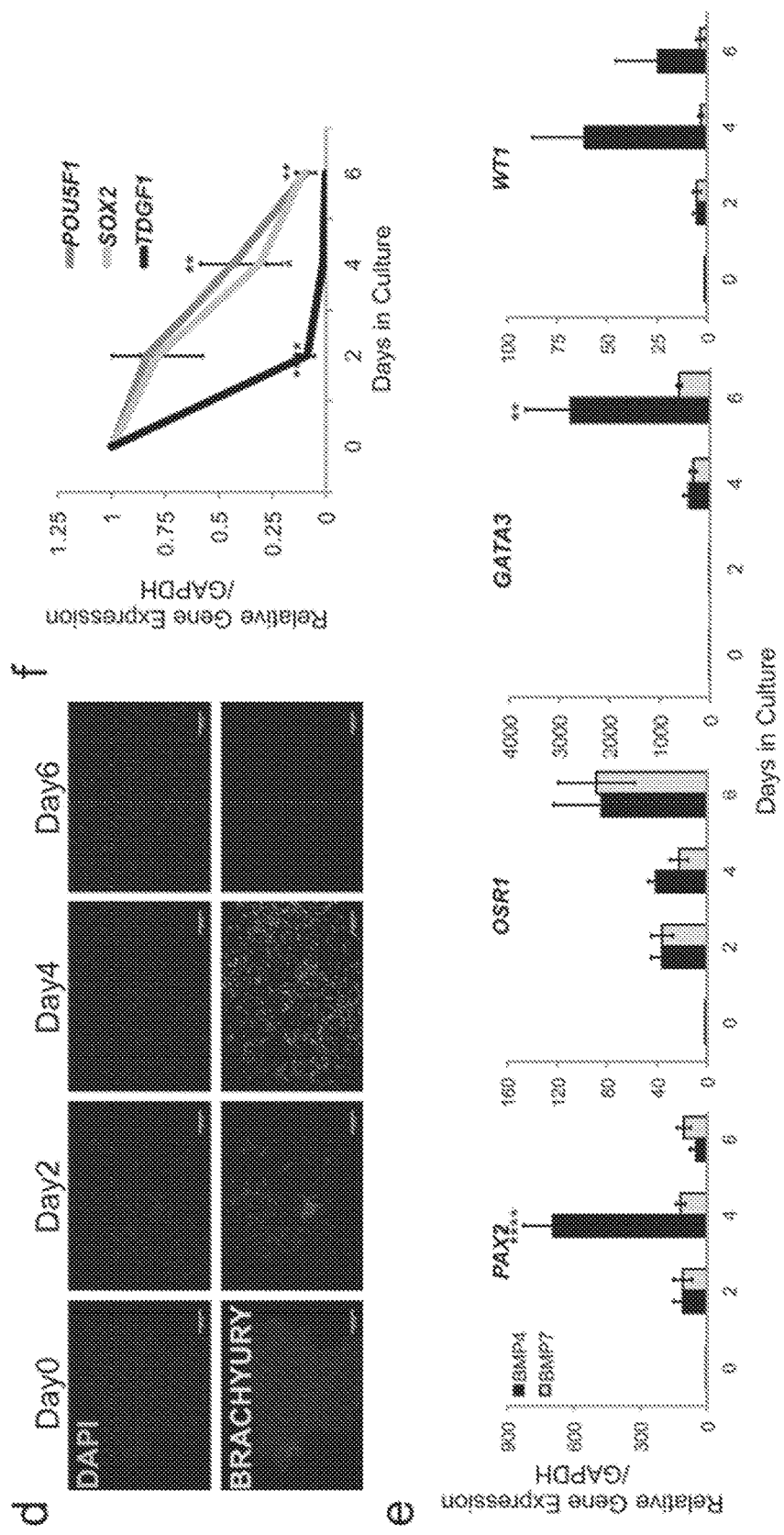

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, N.Y. 2006); Smith, *March's Advanced Organic Chemistry Reactions, Mechanisms and Structure* 7$^{th}$ ed., J. Wiley & Sons (New York, N.Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* 2$^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As described, it is now widely-understood that a majority of high-grade serous carcinomas (HGSC) arise from the secretory cells of the fallopian tube epithelium (FTE). What is needed to build upon these discoveries is relevant in vitro human models that can recapitulate tissue-specific architecture and study early alterations that lead to FTE transformation as well as the initiation and progression of HGSC.

Fallopian tube epithelium (FTE) is composed of a polarized columnar epithelium with multiple cell types including ciliated and secretory cells. Current fallopian tube models, including ex vivo and three-dimensional (3D) spheroid models, demonstrate the importance of the polarity of cells in recreating secretory and ciliated cells. However, FTE cells in these models have a reduced proliferation rate due to induced senescence because of the lack of convoluted luminal architecture and the ectopic microenvironment. Mouse models, including patient-derived xenograft and genetically engineered mice, have overcome some of these limitations and yielded significant insights into the basis of cancer development. However, the complexity of a human tumor is not reliably represented in mouse models. Furthermore, it has been a challenge to engineer silent and expressed mutations with the correct expression timeframe as well as accurate targeting to specific tissue and cell types, such as the secretory cell of the fallopian tube. While biopsy derived 3D human fallopian tube organoid models exists, such approaches are dependent on human biopsy and fallopian tissue with high-risk mutations including BRCA1 cannot be collected for research purposes.

Alternatively, induced pluripotent stem cell (iPSC) technology and 3D-tissue engineering provide powerful tools to recapitulate physiologically relevant aspects of disease progression in vitro and to enhance monolayer cell culture studies. Induced PSCs are generated by reprogramming somatic cells and can be subsequently differentiated into most any cell type. Recently, patient-derived iPSCs have been used to model several inherited human diseases and to successfully generate relevant cell types that displayed disease pathogenesis. However, remaining challenges with iPSC-based modeling include establishing direct differentiation protocols for desired cell types and integrating the cells into functional tissue structures.

Here, the Inventors describe a rapid and efficient method to create an iPSC-derived 3D model of human FTE with the desired cell types and luminal architecture. The female reproductive tract, including FTE, arises from the Müllerian duct in parallel to the urinary system from intermediate mesoderm (IM) of the urogenital ridge in the posterior primitive streak. As such, the Inventors have recapitulated Müllerian development in vitro by starting with established IM protocols and then pro-Müllerian growth factors were used to develop FTE precursors. Correct differentiation was monitored through the expression of cell-related markers such as PAX2, GATA3, OSR1, WT1, and OVGP1. Further differentiation to a FTE lineage was obtained on a 3D growth platform, which enabled the FTE organoid to self-organize into a convoluted luminal structure. Importantly, staining of secretory and ciliated cellular components demonstrated that these structures accurately model fallopian tube function. An iPSC-derived fallopian tube organoid model does not require patient biopsy because the Inventors can generate iPSC from blood cells or skin cells even with known genetic mutations.

Therefore, the Inventors believe the iPSC-derived FTE organoid system could be more beneficial and an ideal platform for identifying the molecular mechanisms leading to early pathogenesis and recapitulating ovarian cancer progression in a controlled environment with high risk mutations.

Described herein is a method for generating a fallopian tube epithelium (FTE), including providing a quantity of human pluripotent stem cells (hPSCs), culturing the hPSCs in the presence of at least one first growth factor and at least one induction molecule to generate mesoderm cells, further culturing the mesoderm cells in the presence of at least one second growth factor, at least one second induction molecule, and at least first one kinase inhibitor to generate intermediate mesoderm (IM) cells, additionally culturing the IM cells in the presence of at least one third growth factor, and at least one second kinase inhibitor to generate Mullerian epithelium cells, and differentiating Mullerian epithelium cells by addition of at least one fourth growth factor into FTE. In other embodiments, the hPSCs are human induced pluripotent stem cells (hiPSCs). In various embodiments, the hiPSCs are obtained from reprogrammed blood cells, including red blood cells, or white blood cells. In various embodiments, the reprogrammed blood cells are from a subject with a hereditary cancer mutation, such as BRCA1. In various embodiments, the hiPSCs possess one or more cancer mutations. In various embodiments, the induction molecule is a GSK-3 inhibitor. In various embodiments, the kinase inhibitor in a RHO kinase inhibitor. In other embodiments, the at least one first growth factor includes activin A, and the at least one induction molecule includes CHIR99021. In various embodiments, the concentration of activin A is 50-150 ng/ml. In various embodiments, the concentration of activin A is 100 ng/ml. In various embodiments, the concentration of CHIR99021 is 1-5 µM. In various embodiments, the concentration of CHIR99021 is 3 µM. In various embodiments, the hPSCs are cultured in a media including DMEM/F12, Glutamax, 500 U/ml penicillin streptomycin (Gibco) and 2% fetal bovine serum (FBS). In other embodiments, culturing the hPSCs includes about 1-0 days. In other embodiments, culturing the hPSCs includes about 2 days. In other embodiments, the at least one second growth factor includes BMP4, the at least one second induction molecule includes CHIR99021, and the at least one first kinase inhibitor includes ROCK inhibitor Y-27632. In various embodiments, the concentration of BMP4 is 50-150 ng/ml. In various embodiments, the concentration of BMP4 is 100 ng/ml. In various embodiments, the concentration of CHIR99021 is 1-5 µM. In various embodiments, the concentration of CHIR99021 is 3 µM. In various embodiments, the concentration of ROCK inhibitor Y-27632 is 1-30 µM. In various embodiments, the concentration of ROCK inhibitor Y-27632 is 10 µM. In various embodiments, the mesoderm cells are culture in a media including DMEM/F12, Glutamax, supplemented with 0.1 mM non-essential amino acids, 500 u/ml penicillin/streptomycin, 0.55 mM 2-mercaptoethanol, and 10% knock-out serum replacement (KOSR). In other embodiments, further culturing the mesoderm cells includes about 1-3 days. In other embodiments, further culturing the mesoderm cells includes about 2 days. In other embodiments, the at least one third growth factor includes WNT4 and at least one second kinase inhibitor includes ROCK inhibitor Y-27632. In various embodiments, the concentration of WNT4 is 50-150 ng/ml. In various embodiments, the concentration of WNT4 is 100 ng/ml. In various embodiments, the concentration of ROCK inhibitor Y-27632 is 1-30 µM. In various embodiments, the concentration of ROCK inhibitor Y-27632 is 10 µM. In various embodiments, the additionally the IM cells are cultured in DMEM/F12, 500 u/ml penicillin/streptomycin, and 10 ml reconstituted Ultroser G serum substitute. In other embodiments, additionally culturing the IM cells includes about 1-3 days. In other embodiments, additionally culturing the IM cells includes about 2 days. In other embodiments, the at least one fourth growth factor includes follistatin estrogen and progesterone. In various embodiments, the concentration of follistatin is 10-30 ng/ml. In various embodiments, the concentration of follistatin is 20 ng/ml. In various embodiments, the concentration of estrogen is 0.1-5 ng/ml. In various embodiments, the concentration of estrogen is 1 ng/ml. In various embodiments, the concentration of progesterone is 10-60 ng/ml. In various embodiments, the concentration of progesterone is 33 ng/ml. In various embodiments, differentiating Mullerian epithelium cells includes about 2 days. In various embodiments, differentiating Mullerian epithelium cells includes about 2-10, 10-20, 20-30, 40-50, 50-60, or 60-70 days. In other embodiments, the IM cells are organized as a spheroid. In other embodiments, spheroids are subsequently cultured in a matrix. In various embodiments, the matrix is Matrigel. In various embodiments, the matrix includes one or more extracellular matrix proteins. In various embodiments, the matrix includes phenol red. In other embodiments, the FTE are organized as an organoid. In other embodiments, the FTE organoids are matured by further culturing for about 10-20, 20-30, 40-50, 50-60, or 60-70 days. In other embodiments, the FTE organoids are matured by further culturing for about 14-65 days. In other embodiments, the FTE organoids are cultured in a condition media from FTE cells freshly isolated from tissue. In other embodiments, mesoderm cells express one or more of: BRACHYURY and MIXL1. In other embodiments, IM cells express one or more of: PAX2, OSR1, GATA3, and WT1. In other embodiments, Mullerian epithelium cells express one or more of: WT1 and OVGP1. In other embodiments, Mullerian epithelium cells do not express one or more of: SIX2, FOXD1, CDX2 and NKX2-1.

Further described herein is a method of generating fallopian tube epithelium (FTE) organoids, providing a quantity of intermediate mesoderm (IM) cells, culturing the IM cells in a matrix and in the presence of at least one first growth factor, and at least first one kinase inhibitor to generate Mullerian epithelium cells, and differentiating Mullerian epithelium cells by addition of at least one second growth factor into FTE organoids. In other embodiments, the at least one first growth factor includes WNT4 and at least one kinase inhibitor includes ROCK inhibitor Y-27632. In various embodiments, the concentration of WNT4 is 50-150 ng/ml. In various embodiments, the concentration of WNT4 is 100 ng/ml. In various embodiments, the concentration of ROCK inhibitor Y-27632 is 1-30 µM. In various embodiments, the concentration of ROCK inhibitor Y-27632 is 10 µM. In other embodiments, culturing the IM cells includes about 2 days. In other embodiments, the at least one second growth factor includes follistatin estrogen and progesterone. In various embodiments, the concentration of follistatin is 10-30 ng/ml. In various embodiments, the concentration of follistatin is 20 ng/ml. In various embodiments, the concentration of estrogen is 0.1-5 ng/ml. In various embodiments, the concentration of estrogen is 1 ng/ml. In various embodiments, the concentration of progesterone is 10-60 ng/ml. In various embodiments, the concentration of progesterone is 33 ng/ml. In various embodiments, differentiating Mullerian epithelium cells includes about 2 days. In various embodiments, differentiating Mullerian epithelium cells includes about 2-10, 10-20, 20-30, 40-50, 50-60, or 60-70 days. In other embodiments, the IM cells are organized as a spheroid. In other embodiments, spheroids are subsequently cultured in a matrix. In various embodiments, the matrix is Matrigel. In various embodiments, the matrix includes one or more extracellular matrix proteins. In various embodiments, the matrix includes phenol red. In other embodiments, the FTE organoids are matured by further culturing for about 14-65 days. In other embodiments, the FTE organoids are cultured in a condition media from FTE cells freshly isolated from tissue. In other embodiments, the FTE organoids express one or more of: TUBB4A, FOXJ1, PAX8 and CDH1. In various embodiments, the organoids include ciliary, luminal and/or secretory structures.

Also described herein is a quantity of fallopian tube epithelium (FTE) organoids made by a method including generating fallopian tube epithelium (FTE) organoids, providing a quantity of intermediate mesoderm (IM) cells, culturing the IM cells in a matrix and in the presence of at least one first growth factor, and at least first one kinase inhibitor to generate Mullerian epithelium cells, and differentiating Mullerian epithelium cells by addition of at least one second growth factor into FTE organoids. In other embodiments, the at least one first growth factor includes WNT4 and at least one kinase inhibitor includes ROCK inhibitor Y-27632. In various embodiments, the concentration of WNT4 is 50-150 ng/ml. In various embodiments, the concentration of WNT4 is 100 ng/ml. In various embodiments, the concentration of ROCK inhibitor Y-27632 is 1-30 µM. In various embodiments, the concentration of ROCK inhibitor Y-27632 is 10 µM. In other embodiments, culturing the IM cells includes about 2 days. In other embodiments, the at least one second growth factor includes follistatin estrogen and progesterone. In various embodiments, the concentration of follistatin is 10-30 ng/ml. In various embodiments, the concentration of follistatin is 20 ng/ml. In various embodiments, the concentration of estrogen is 0.1-5 ng/ml. In various embodiments, the concentration of estrogen is 1 ng/ml. In various embodiments, the concentration of progesterone is 10-60 ng/ml. In various embodiments, the concentration of progesterone is 33 ng/ml. In various embodiments, differentiating Mullerian epithelium cells includes about 2 days. In various embodiments, differentiating Mullerian epithelium cells includes about 2-10, 10-20, 20-30, 40-50, 50-60, or 60-70 days. In other embodiments, the IM cells are organized as a spheroid. In other embodiments, spheroids are subsequently cultured in a matrix. In various embodiments, the matrix is Matrigel. In various embodiments, the matrix includes one or more extracellular matrix proteins. In various embodiments, the matrix includes phenol red. In other embodiments, the FTE organoids are matured by further culturing for about 14-65 days. In other embodiments, the FTE organoids are cultured in a condition media from FTE cells freshly isolated from tissue. In other embodiments, the FTE organoids express one or more of: TUBB4A, FOXJ1, PAX8 and CDH1. In various embodiments, the organoids include ciliary, luminal and/or secretory structures.

Further described herein is a composition of fallopian tube epithelium (FTE) organoids. Also described herein is a pharmaceutical composition, including a composition of FTE organoids and a pharmaceutically acceptable carrier. In various embodiments, the FTE organoids are derived from human pluripotent stem cells, including are human induced pluripotent stem cells (hiPSCs). In various embodiments, the hiPSCs are obtained from reprogrammed blood cells, including red blood cells, or white blood cells. In various embodiments, the reprogrammed blood cells are from a subject with a hereditary cancer mutation, such as BRCA1. In various embodiments, the hiPSCs possess one or more cancer mutations.

Also described herein is a method including selecting a subject in need of treatment for a reproductive tract disease and/or condition, administering to the subject a quantity of fallopian tube epithelium (FTE) cells, wherein the FTE cells are capable of treating the reproductive tract disease and/or condition. In various embodiments the reproductive tract disease includes the upper reproductive tract, including fallopian tubes, ovary and uterus. In various embodiments, the reproductive tract disease and/or condition includes damage and/or dysfunction in the reproductive tract. This includes for example, damage and/or dysfunction associated with endometriosis, uterine fibroids, pelvic inflammatory disease, polyps, scarring, unusual shape. In various embodiments, the treatment of the reproductive tract disease includes FTE cells repairing, regenerating cellular structures in the reproductive tract, and/or restoring functional capabilities of existing cells in the reproductive tract.

EXAMPLE 1 iPSC Culture

Human B-cells, mammary epithelial cells and fibroblasts were used to derive iPSCs, which were cultured in mTeSR®1 medium (STEMCELL) on growth factor-reduced Matrigel™ Matrix (BD Biosciences)-coated plates at 37° C. in a 5% $CO_2$ incubator. Briefly, 70-90% confluent human iPSC colonies were dissected into small squares using the EZ Passage tool (Invitrogen). For weekly passaging, colonies were lifted carefully with a cell scraper, removed using a 5 ml glass pipette, and replated at a 1:6 ratio.

EXAMPLE 2

Directed Differentiation of iPSCs in Chemically Defined Conditions

Human iPSCs were split onto Matrigel-coated plates, and cultured in mTeSR®1 medium until 80% confluent. Three intermediate protocols were compared, according to Mae et al. (2013), Xia et al. (2013), and Takasato et al. (2014). The final protocol that achieved best efficiency and results for creating fallopian tube epithelium was a modified Mae et. al., (2013) protocol, as defined below.

Day 0-2: Cells were exposed to 100 ng/ml human recombinant activin A (Stemgent) and 3 µM CHIR99021 (Cayman Chemicals) to differentiate towards mesoderm, and cultured in DMEM/F12 (Gibco)+Glutamax (Invitrogen) supplemented with 500 U/ml penicillin streptomycin (Gibco) and 2% fetal bovine serum (FBS) with addition of 10 µM ROCK inhibitor Y-27632 (Stemgent).

Day 2-4: To differentiate towards IM, media was changed to DMEM/F12 (Gibco)+Glutamax (Invitrogen) supplemented with 0.1 mM non-essential amino acids (Invitrogen), 500 u/ml penicillin/streptomycin (Gibco), 0.55 mM 2-mercaptoethanol, 10% KOSR (Invitrogen), 100 ng/ml BMP4 (R&D Systems), 3 µM CHIR99021 (Cayman Chemicals), and 10 µM ROCK inhibitor Y-27632 (Stemgent).

Day 4-6: Spheroids were collected from wells and re-plated per methods described below. To differentiate the spheroid cultures towards Müllerian epithelium, media was changed to Fallopian tube media (FTM) containing DMEM/F12 (Gibco)+500 u/ml penicillin/streptomycin (Gibco), and 10 ml reconstituted Ultroser G (15950-017, Pall) and 10 µM ROCK inhibitor Y-27632 (Stemgent). To the FTM, 100 ng/ml human recombinant WNT4 (R&D Systems) with or without 3 µM CHIR99021(Cayman Chemicals), 100 ng/ml human recombinant WNT3A (R&D Systems) with or without 3 µM CHIR99021 (Cayman Chemicals) were added.

Day 6-8: FTM was changed and 20 ng/ml human recombinant Follistatin (Peprotech), 1 ng/ml estrogen and 33 ng/ml progestrone were added.

EXAMPLE 3

Growing FTE Organoids from Spheroids in Matrigel

Spheroids were collected on day 4 from every well under a stereomicroscope using a 200 µl barrier pipette tip and pooled into a 1.5 ml microcenterfuge tube. Spheroids were then mixed with 50 µl Matrigel (BD Biosciences) containing estrogen (1 ng/ml) and progesterone (33 ng/ml), and slowly pipetted into the middle of one well of a 24-well Nunclon delta surface dish. The 3D droplet was allowed to solidify for 10-15 minutes in a tissue incubator, and Matrigel beads were then bathed in FTM supplemented with the same concentration of growth factors. Media was replaced every 3-4 days as necessary and cells were replated every two weeks.

EXAMPLE 4

RNA Isolation and Real-Time PCR Analysis

Total cellular RNA was isolated using Qiagen RNeasy Mini kit according to the manufacturer's recommendations (Qiagen). Of RNeasy-treated total RNA (1 µg) was used for cDNA synthesis using the Quantitect Reverse Transcription Kit for cDNA synthesis for PCR (Qiagen). Real-time PCR was performed using the SYBR Green Supermix (BioRad). The levels of expression of respective genes were normalized to corresponding GAPDH values and are shown as fold change relative to the value of the control sample. All sample analyses were carried out in triplicate. The list of primers used for real-time PCR experiments are listed in Table 1.

TABLE 1

| RT-PCR PRimers | | |
| --- | --- | --- |
| Primer | Forward | Reverse |
| BRACHYURY | GCTGTGACAGGTACCCAACC [SEQ ID NO: 1] | CATGCAGGTGAGTTGTCAGAA [SEQ ID NO: 2] |
| FOXD1 | GACTCTGCACCAAGGGACTG [SEQ ID NO: 3] | CAATTGGAAATCCTAGCAGTAAAGT [SEQ ID NO: 4] |
| FOXJ1 | GGGGTGGGAGCAACTTCT [SEQ ID NO: 5] | CCTCCTCCGAATAAGTATGTGGT [SEQ ID NO: 6] |
| GAPDH | GTGGACCTGACCTGCCGTCT [SEQ ID NO: 7] | GGAGGAGTGGGTGTCGCTGT [SEQ ID NO: 8] |
| GATA3 | CTCATTAAGCCCAAGCGAAG [SEQ ID NO: 9] | GTCTGACAGTTCGCACAGGA [SEQ ID NO: 10] |
| HOXB7 | CCGAGAGTAACTTCCGGATCTA [SEQ ID NO: 11] | CGTCAGGTAGCGATTGTAGTGA [SEQ ID NO: 12] |
| MIXL1 | GGTACCCCGACATCCACTT [SEQ ID NO: 13] | GCCTGTTCTGGAACCATACCT [SEQ ID NO: 14] |
| NCAM | GATTCCTCCTCCACCCTCAC [SEQ ID NO: 15] | CAATATTCTGCCTGGCCTGG [SEQ ID NO: 16] |
| NKX2.1 | TCATTTGTTGGCGACTGG [SEQ ID NO: 17] | TGCTTTGGACTCATCGACAT [SEQ ID NO: 18] |
| OSR1 | GGACCTCTGCGGAACAAG [SEQ ID NO: 19] | TGCAGGGAAGGGTGGATA [SEQ ID NO: 20] |
| OVGP1 | AAGCTGTTGCTGTGGGTTG [SEQ ID NO: 21] | TGTGCCCAGTTGGTGAAAT [SEQ ID NO: 22] |
| OVGP1-2 | AATTCTCTACCCAGAGTTCAACAA A [SEQ ID NO: 23] | CCGATGGACAGTAGTGTTTTCA [SEQ ID NO: 24] |
| PAX2 | GAAGTGCCCCCTTGTGTG [SEQ ID NO: 25] | TCGTTGTAGGCCGTGTACTG [SEQ ID NO: 26] |
| POU5F1 | ACCCACACTGCAGCAGATCA [SEQ ID NO: 27] | CCACACTCGGACCACATCC [SEQ ID NO:28] |

TABLE 1-continued

RT-PCR PRimers

| Primer | Forward | Reverse |
|---|---|---|
| SALL1 | ATTGCAGCCTAGCCAAAAAG [SEQ ID NO: 29] | ACCAGCTGAGCAGAAAGGTC [SEQ ID NO: 30] |
| SIX2 | CAGGTCAGCAACTGGTTCAA [SEQ ID NO: 31] | AGCTGCCTAACACCGACTTG [SEQ ID NO: 32] |
| SOX17 | ACGCCGAGTTGAGCAAGA [SEQ ID NO: 33] | TCTGCCTCCTCCACGAAG [SEQ ID NO: 34] |
| SOX2 | GGGGGAATGGACCTTGTATAG [SEQ ID NO: 35] | GCAAAGCTCCTACCGTACCA [SEQ ID NO: 36] |
| TDGF1 | AGGGAACAATGACAGAGTGTGA [SEQ ID NO: 37] | CCC GAGATGGACGAGCAAAT [SEQ ID NO: 38] |
| TNFaIP2 | GAGCCACGGCTTTGACAC [SEQ ID NO: 39] | GTGCGTGAACCTCTTGAACA [SEQ ID NO: 40] |
| WT1 | GAATGCATGACCTGGAATCA [SEQ ID NO: 41] | TCTGCCCTTCTGTCCATTTC [SEQ ID NO: 42] |

TABLE 2

Cell Background Information.

| Cell ID | Parent Tissue | Biopsy | Gender | Karyotype |
|---|---|---|---|---|
| 87iCTR-n3 | EBV B-cell | Blood | female | normal |
| 01iMEC-n4 | Mammary epithelial cells | Mammary epithelial | female | normal |
| 14iCTR-n6 | Fibroblast | Skin | female | normal |

EXAMPLE 5

Immunocytochemistry for Monolyer Culture

Monolayer cultures were grown on poly-1-lysine and ornithine coated glass coverslips. Cells were washed once with phosphate buffered saline (PBS) and fixed with 4% paraformaldehyde (PFA) in 1× PBS for 20 minutes and permeabilized in PBS containing 0.5% Triton X-100 (PBS-T) (Sigma) for 5 minutes at room temperature. Cells were then, blocked with 10% FBS in PBS for 1 hour at room temperature, and followed by 2 hour incubation in primary antibodies (see below section). The cultures were washed with PBS-T three times for 15 minutes each at room temperature and incubated with species-specific AF488 or AF594-conjugated secondary antibodies followed by the nuclei counterstain with DAPI. Following three washes in PBS-T, the coverslips were mounted onto glass slides and were imaged using Nikon/Leica microscopes. Each selected image is representative of a minimum of three independent experiments with at least two technical duplicates.

EXAMPLE 6

Immunocytochemistry for Organoid and Fallopian Tube Tissue

Organoids and fallopian tube tissues were fixed with 4% PFA in 1× PBS for 20 minutes, followed by three PBS washes. The fixed organoids and fallopian tube tissues were then sunk in 30% sucrose at 4° C. overnight and then embedded into OCT (Tissue-Tek). Frozen sections were collected at 12 μm using a cryostat onto glass slides and stored at −80° C. Each section was rehydrated with 1× PBS for 5 min and blocked in a solution of 10% FBS in PBS+0.05% Triton X-100 (PBS-T) for 1 hour at room temperature, followed by 2 hour incubation at room temperature in primary antibodies (see below section) in blocking solution. The slides were washed with PBS-T three times for 15 minutes each at room temperature and incubated with species-specific AF488 or AF594-conjugated secondary antibodies followed by DAPI counterstain. Following three washes in PBS-T, the tissue was covered with a glass slide and imaged using Nikon/Lecia microscopes. Each image selected for figures of this manuscript is representative of a minimum of three independent experiments with at least two technical duplicates.

EXAMPLE 7

Antibodies

The following primary antibodies were used for fluorescence microscopy experiments at 1:200 dilution and secondary antibodies at 1:400 dilution: WT1 (Abcam, ab89901), PAX8 (Proteintech, 21384-1-AP), TUBB4A (Abcam, ab1315), BRACHYURY (Abcam, ab20680), POU5F1 (Stemgent, 09-0023), Nanog (Stemgent, 09-0020), SOX2 (Stemgent, 09-0024), TRA-1-60 (Stemgent, 09-0010), TRA-1-81 (Stemgent, 09-0011), SSEA4 (Stemgent, 09-0006), CDX2 (Biocare Medical, CM226A), SIX2 (Proteintech, 11562-1-AP), FOXJ1 (Abcam, ab40869), CDH1 (R&D System, AF648), OVGP1 (SIGMA, HPA062205) and DAPI (Molecular Probes, D3571).

EXAMPLE 8

Fallopian Tube Tissue Collection

Fallopian tubes were collected from patients undergoing surgery for benign gynecological indications, such as adnexal mass, fibroids, or other conditions not affecting the fallopian tubes. Tissue collection was under IRB PRO00033469. Tissues were inspected and confirmed by pathology to be healthy and not associated with gynecologic malignancy. Upon surgical excision, fallopian tubes were collected in warmed sterile FTM as defined above. Fallopian tubes were rinsed 2 times for 10 mins with Red Blood Cell (RBC) lysis buffer (0.144M $NH_4Cl$ and 0.014M $NH_4HCO_3$ in 10:1 ratio).

EXAMPLE 9

Statistical Analysis

Statistical analyses were performed by using Prism software (GraphPad Software, La Jolla, Calif.). All quantitative data were expressed as mean values±Standard Error of the Mean (SEM) and analyzed by analysis of variance (ANOVA) followed by a Tukey post-hoc analysis of mean differences in three biological replicates. Differences were considered significant at *$p \leq 0.05$, $p \leq 0.01$, *$p \leq 0.001$, ****$p \leq 0.0001$.

EXAMPLE 10

Robust Differentiation of Human iPSCs into Intermediate Mesoderm-Like Cells

The mesoderm differentiates into the IM, in a sequential manner determined by the differential expression of specific transcription factors in response to signaling pathways, including WNT, Nodal/Activin and Bone Morphogenetic Proteins (BMPs) (FIG. 1a, b). The IM subsequently develops in parallel into both the FTE and kidney. At 6 weeks post-fertilization, mesonephric ducts are formed and develop separately into the Müllerian ducts. There are several protocols for kidney development, which primarily utilize signaling molecules in various temporal combinations (FIG. 1b). However, no successful protocol exists, to date, for iPSC development into fallopian tube.

Figure 4:
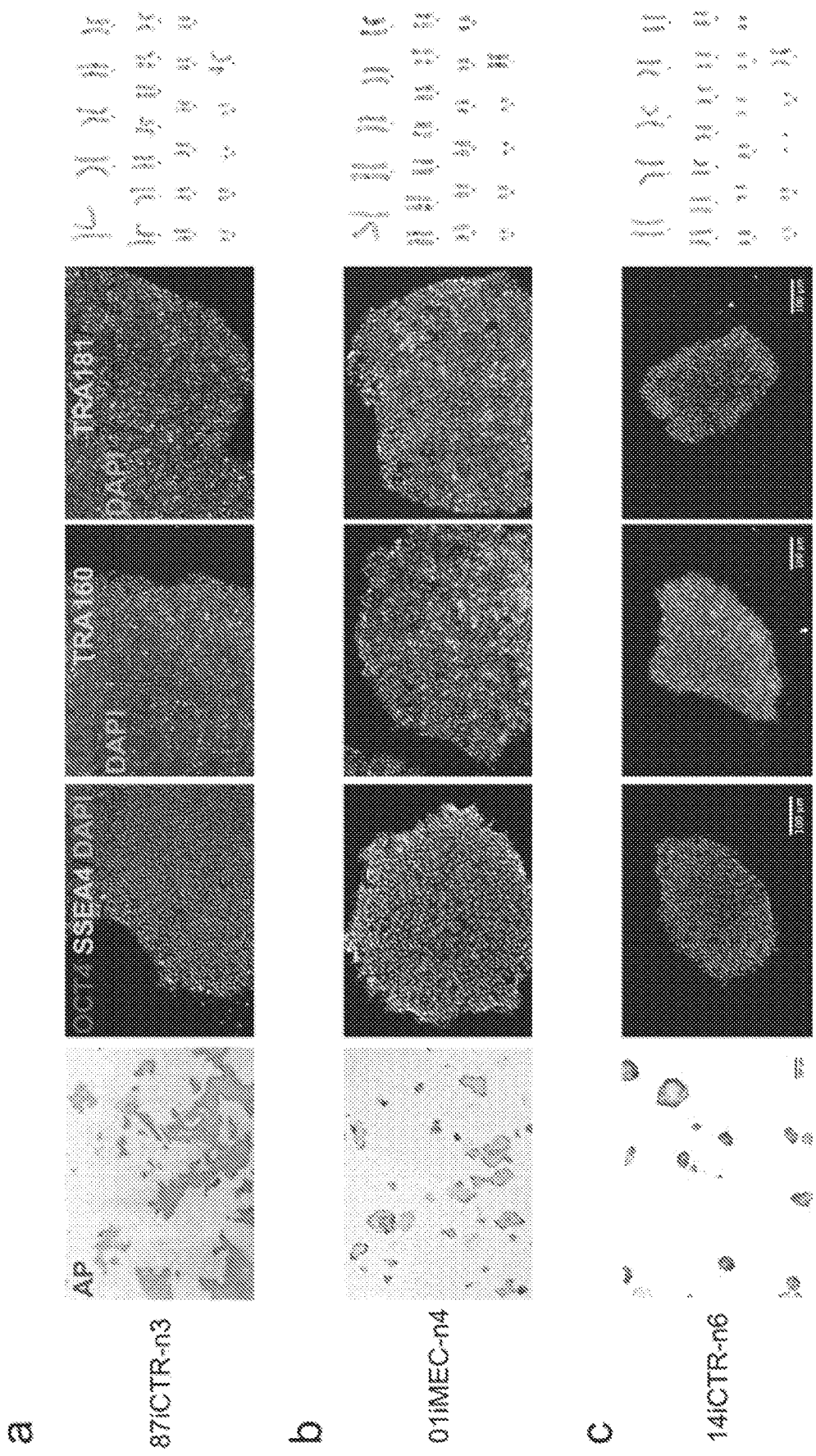
FIG. 4: Characterization of iPSC lines. All characterized iPSC lines (87iCTR-n3, 01iMEC-n4 and 14iCTR-n6) express pluripotent stem cell markers a) Alkaline Phosphatase (AP) and b) for OCT4, NANOG, SOX2, TRA160, TRA181, SSEA4 based on immunocytochemistry, as well as c) exhibit a normal karyotype based on G-band analysis.
Figure 5:
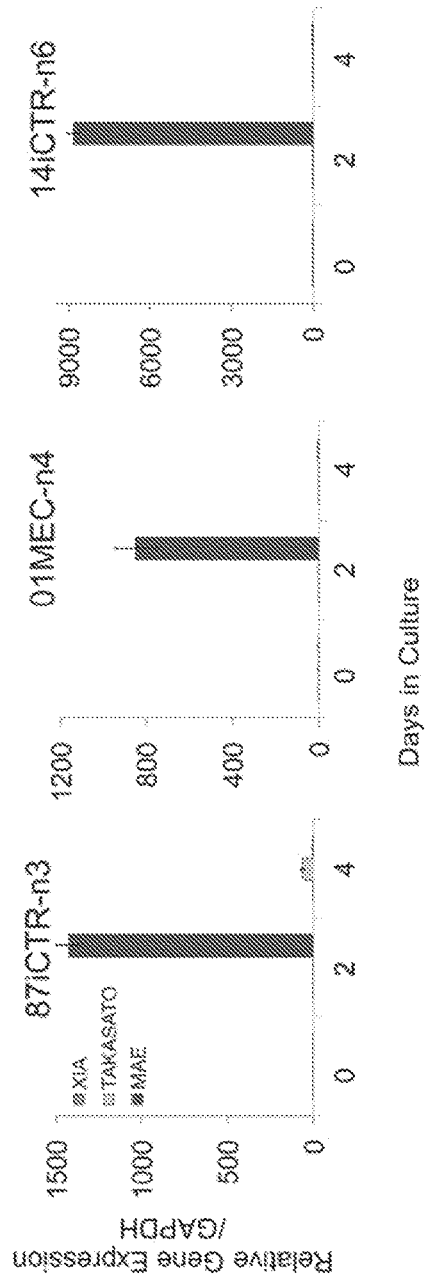
FIG. 5: IM differentiation efficiency for established protocols. Expression kinetics of mesoderm markers a) MIXL1- and b) BRACHYURY during the 6-day differentiation course of iPSC lines 87iCTR-n3, 01iMEC-n4 and 14iCTR-n6 using protocols from Xia, Y. et al. Directed differentiation of human pluripotent cells to ureteric bud kidney progenitor-like cells. Nat Cell Biol 15, 1507-1515, doi:10.1038/ncb2872 (2013)., Mae et. al. (2013), Takasato, M. et al. Directing human embryonic stem cell differentiation towards a renal lineage generates a self-organizing kidney. Nat Cell Biol 16, 118-126, doi:10.1038/ncb2894 (2014).
Figure 5:
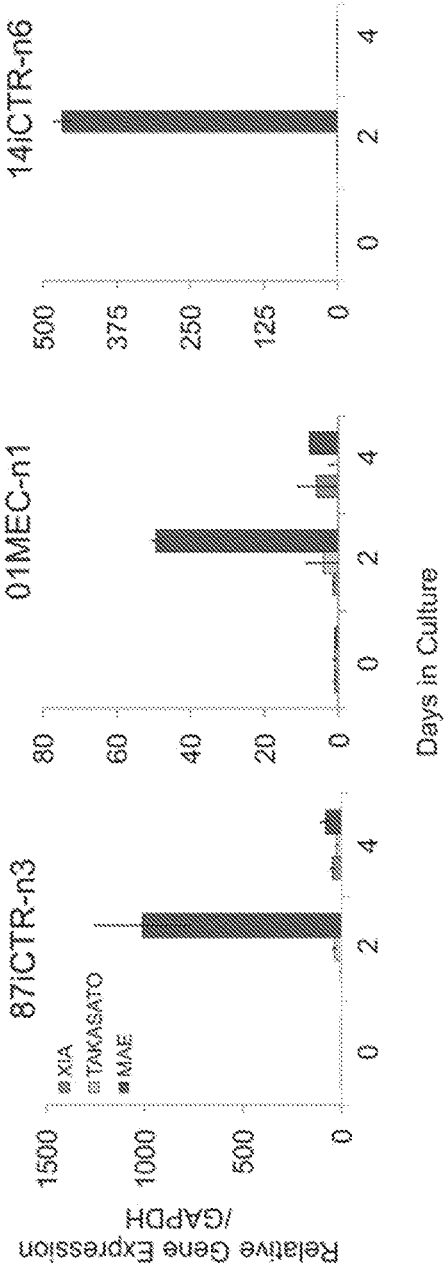

In order to create a specific 3D iPSC-derived model of FTE, the Inventors used three different human iPSC lines (87iCTR-n3, 01iMEC-n4, 14iCTR-n6) that were reprogrammed initially from B-cells, mammary epithelial cells and fibroblasts, respectively. Each line demonstrated the molecular hallmarks of pluripotent cells, including morphology, normal karyotype, alkaline phosphatase expression and pluripotency markers (FIG. 4), and they were able to differentiate into all three embryonic germ layers (data not shown). The ideal IM differentiation platform was first established by investigating three published protocols for directed differentiation of iPSCs into kidney progenitor cells[21-23]. To determine the efficiency of mesoderm induction, PCR and immunocytochemistry were used to assess early mesoderm specific transcription factors MIXL1 and BRACHYURY. A protocol with 100 ng/ml of activin A and 3 µM of CHIR99021 rapidly and efficiently specified human iPSCs (line 87iCTR-n3) into mesoderm, which recapitulates Mae et al (2013) (FIG. 1c). All three human iPSC lines (87iCTR-n3, 01iMEC-n4, 14iCTR-n6) showed a similar pattern, though the differentiation potential varied slightly between lines (FIG. 5). The peak of BRACHYURY and MIXL1 expression at day 2 followed by subsequent downregulation is consistent with the transient expression of these genes during gastrulation. In addition, BRACHYURY protein production showed a similar kinetic pattern during cell differentiation (FIG. 1d).

Figure 6:
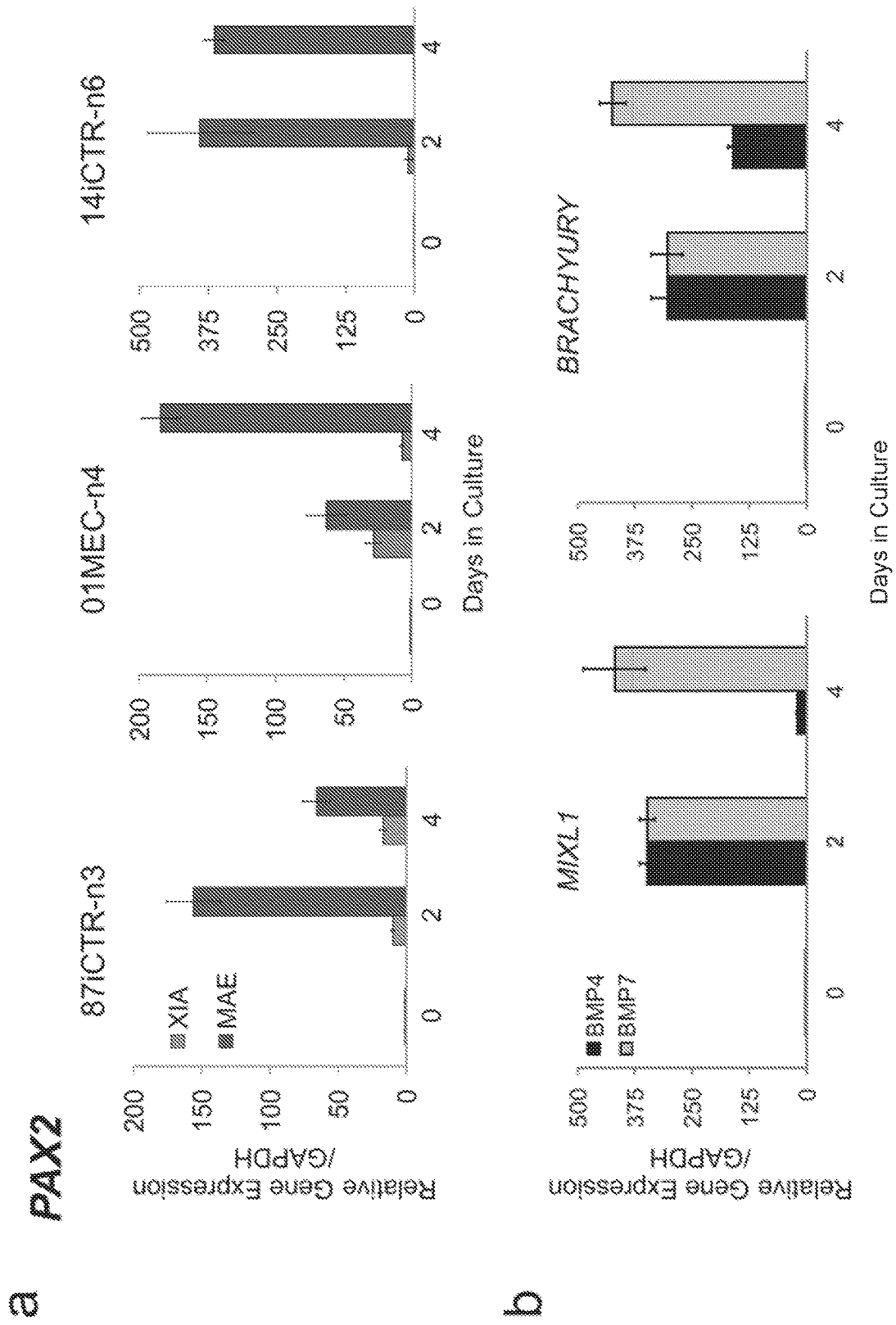
FIG. 6: Substitution to Mae et al. protocol with BMP4 from BMP7. a) Expression of intermediate mesoderm marker, PAX2, during the 6-day differentiation course of iPSC lines 87iCTR-n3, 01iMEC-n4 and 14iCTR-n6 using protocols from Xia et. al. (2013) and Mae et. al. (2013). b) Expression kinetics of mesoderm markers MIXL1- and BRACHYURY during differentiation with BMP4 vs BMP7 treatment for 87iCTR-n3 iPSC line. c) Expression kinetics of ectoderm marker NCAM and endoderm marker SOX17 during differentiation with BMP4 vs BMP7 treatment for 87iCTR-n3 iPSC line.
Figure 6C:
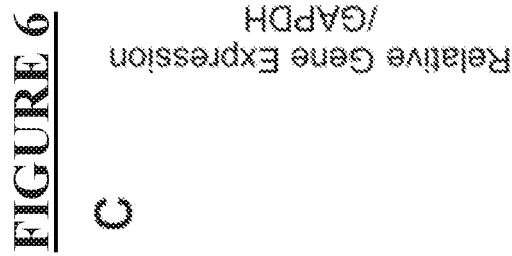

The BMP signaling pathway, known to regulate mesodermal cell determination, was next examined to further specify mesoderm differentiation into IM. While the Mae et al (2013) protocol uses BMP7, results here showed that exposure to 100 ng/ml of BMP4 provided optimal mesoderm differentiation into IM, based on expression levels of early IM markers PAX2, OSR1 and GATA3 (FIG. 1e). Once again, all three human iPSC lines showed a similar pattern of differentiation based on PAX2 expression, with slightly varying levels of differentiation between lines (FIG. 6a). As in FIG. 1c, BMP4 provided the expected transient upregulation of BRACHYURY and MIXL1 seen during gastrulation, which was not recapitulated with BMP7 treatment (FIG. 6b). Importantly, BMP4 has been shown to regulate early ovarian follicle development and the creation of neonatal mouse uterine epithelium. Notably, BMP4-induced IM was more prone to differentiate towards FTE compared to BMP7, as suggested by the intermediate upregulation of markers primed for the female reproductive tract, namely WT1 (FIG. 1e). In parallel to mesoderm and IM gene induction, the expression of pluripotency genes POU5F1, SOX2 and TDGF1 was reduced (FIG. 1f). This new differentiation protocol that included BMP4 appears to be mostly specific for mesoderm, as there was no to very low detectable expression levels for the endoderm-marker SOX17 and the ectoderm-marker NCAM (FIG. 6c).

Collectively, these data show that human iPSCs can be differentiated into mesoderm and IM. Critically, compared to other tested protocols, this newly developed protocol with BMP4 yielded the highest level of mesoderm and IM differentiation.

EXAMPLE 11

Differentiation of Intermediate Mesoderm into Fallopian Tube Epithelial

Figure 2:
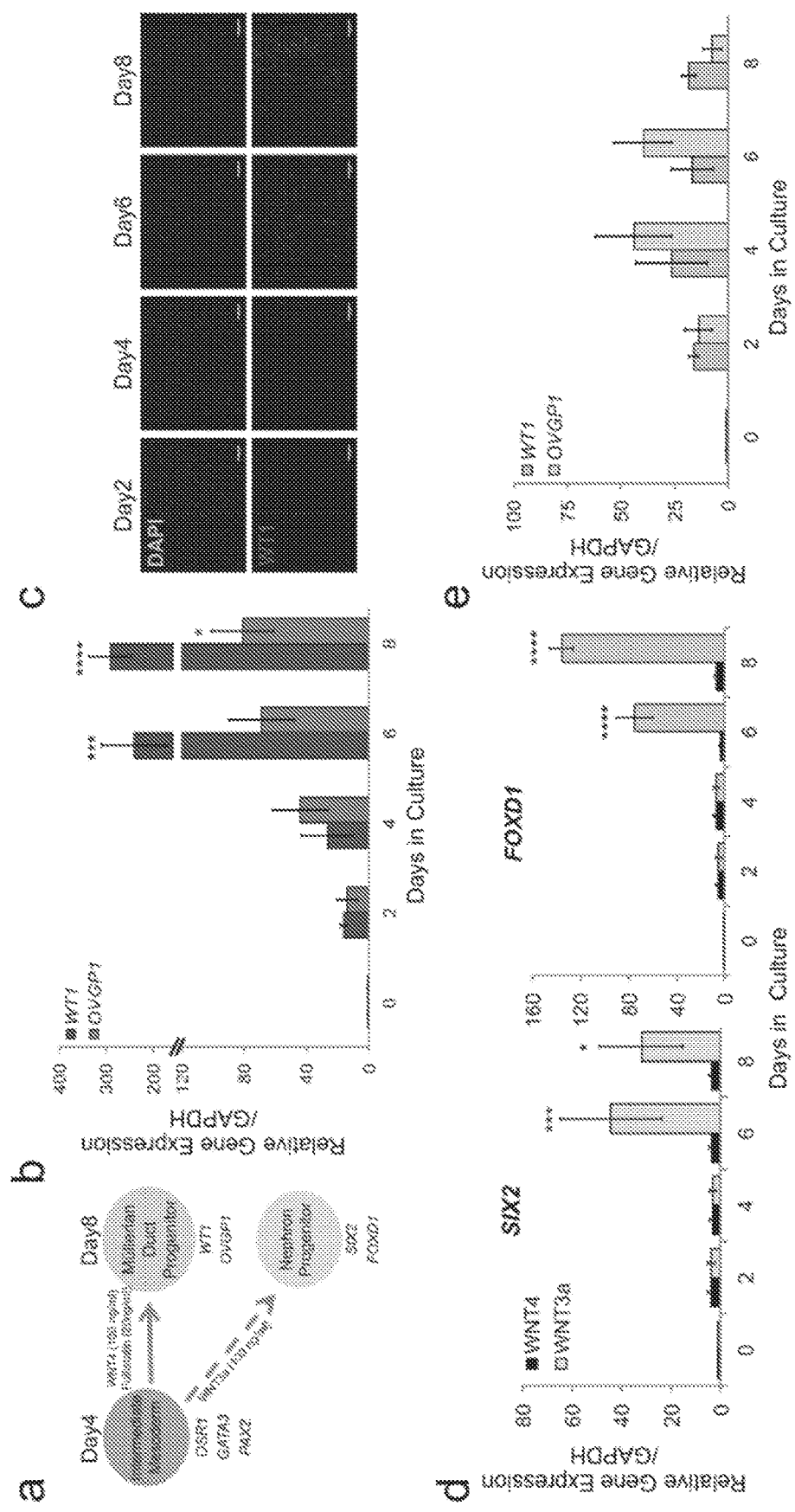
FIG. 2: Differentiation of Intermediate Mesoderm into Fallopian Tube Epithelium Cell. a) Timeline and factors involved in the differentiation of intermediate mesoderm into fallopian tube epithelium precursor cells. b) qPCR quantification of gene expression kinetics for Müllerian duct markers. WT1 and OVGP1, throughout Müllerian duct differentiation. c) Immunocytochemistry demonstrating protein production and localization of WT1 during Müllerian duct differentiation. d) mRNA fold change comparison of kidney markers SIX2 and FOXD1 in response to Müllerian (WNT4, black bars) vs nephric duct (WNT3a, grey bars) differentiations. e) qPCR quantification of gene expression kinetics for Müllerian duct markers, WT1 and OVGP1, throughout the nephric duct differentiation. Relative gene expression to iPSC stage (Day 0) was calculated using $\Delta\Delta$Ct method and normalized endogenous GAPDH level for 87iCTR-n3 iPSC line. Error bars are SEM (n=3 independent experiments). ANOVA with Tukey post-hoc test was used for this analysis, with significance at $*p \leq 0.05$, $*p \leq 0.001$, $**p \leq 0.0001$.
Figure 7:
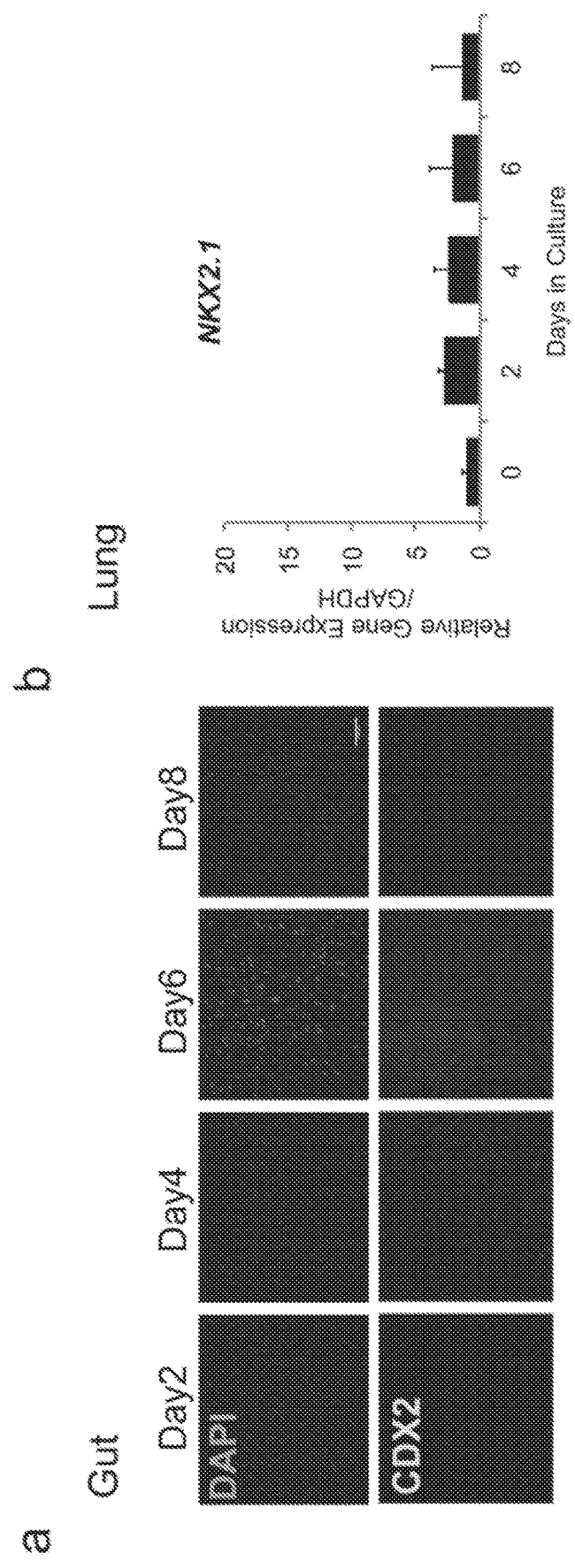
FIG. 7: Immunocytochemistry analysis throughout the Müllerian duct differentiation for production of a) gut marker CDX2 and b) lung marker NKX2.1.
Figure 8:
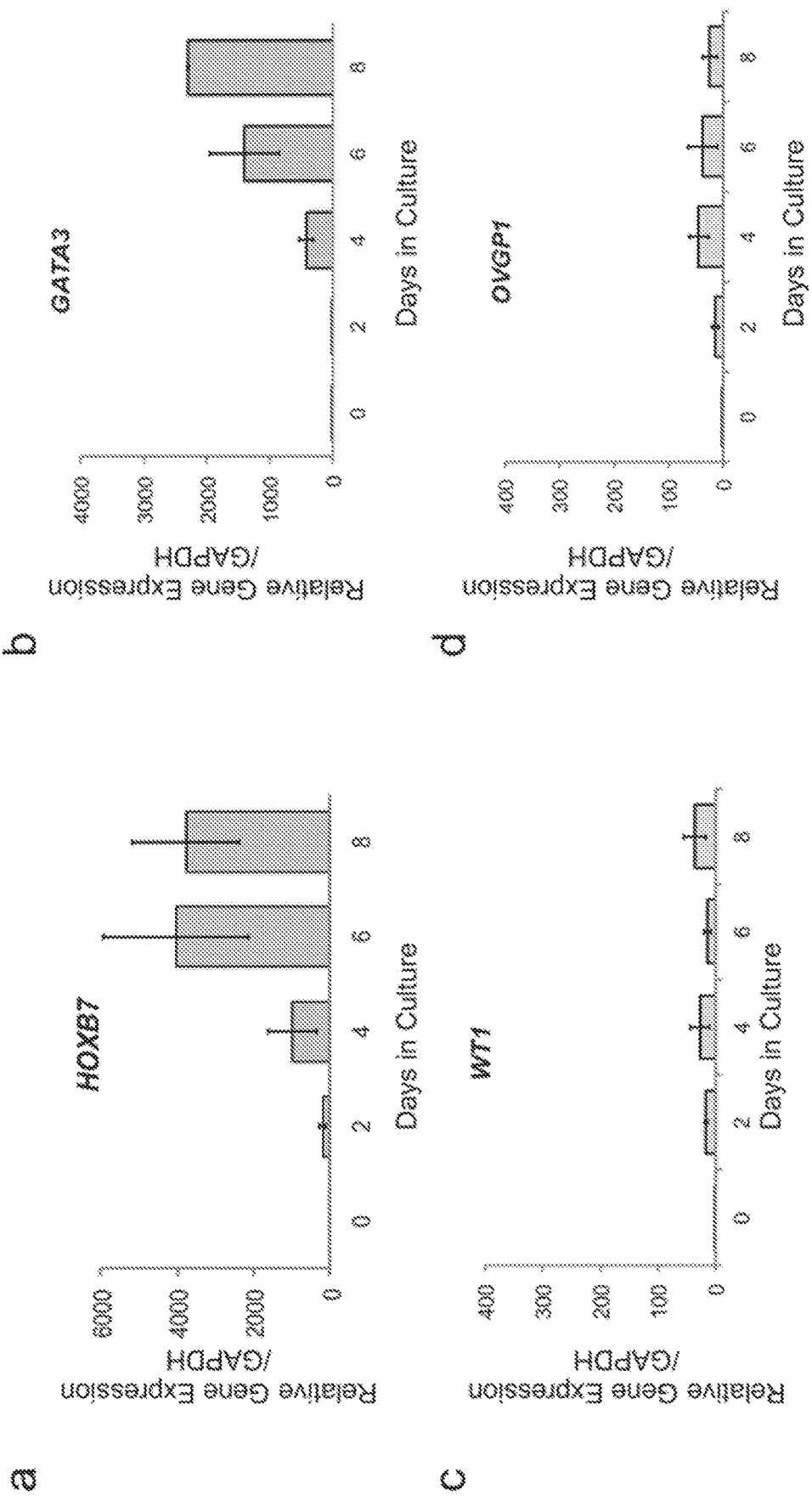
FIG. 8: Expression kinetics of a,b) early mesonephric duct markers HOXB7 and GATA3, c,d) Müllerian duct markers WT1 and OVGP1 and e,f) kidney markers SIX2 and FOXD1 with WNT4/CHIR99021 treatment of the 87iCTR-n3 iPSC line.
Figure 8:
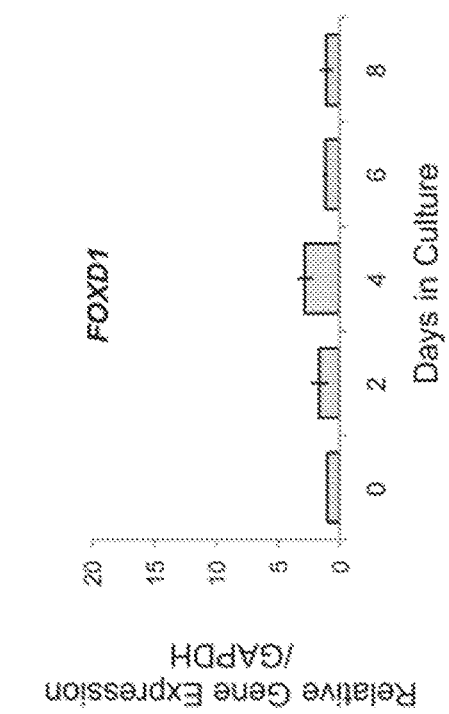
Figure 8:

Female tract differentiation requires WNT4 for initiation and elongation phases of Müllerian duct formation and subsequently requires the downstream component, Follistatin, to form the Müllerian duct. In order to differentiate IM into FTE, cultures were treated with 100 ng/ml of WNT4 on day 4 followed by 20 ng/ml of Follistatin on day 6 (FIG. 2a). Müllerian duct formation was confirmed by both PCR and immunocytochemistry, which showed upregulated expression over time of the fallopian tube precursor markers WT1 and OVGP1 (FIG. 2b-c). Importantly, this protocol was specific to Müllerian duct differentiation, given the lack of expression of the kidney markers SIX2 and FOXD1 (FIG. 2d, black bars), as well as the intestinal and lung markers CDX2 and NKX2-1, respectively (FIG. 7a,b). Interestingly, WNT4 along with prolonged CHIR99021 exposure led to the expression of early mesonephric duct markers HOXB7 and GATA3 (FIG. 8a,b). However, compared to WNT4 alone (FIG. 2b), FTE markers WT1 and OVGP1 did not show increased expression (FIG. 8c,d). Additionally, as with WNT4 alone (FIG. 2d), WNT4/CHIR did not induce expression of kidney progenitor markers SIX2 and FOXD1 (FIG. 8e,f). This suggests that continued CHIR99021 during WNT4 treatment might induce other WNT signaling factors that actually disrupt further Müllerian development.

Figure 11:
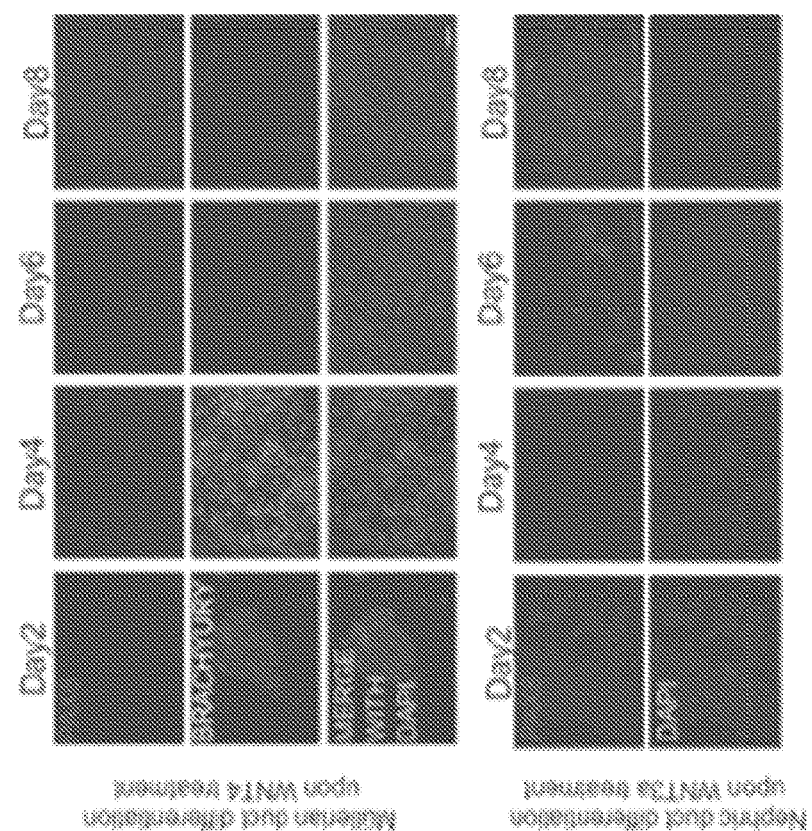
FIG. 11: PAX8 expression pattern during the course of differentiation: a) qPCR quantification of gene expression kinetics for PAX8 in response to Müllerian (WNT4, black bars) vs nephric duct (WNT3a, gray bars) differentiation. b) Immunocytochemistry demonstrating PAX8 expression during Müllerian duct differentiation. c) Immunocytochemistry demonstrating protein production and localization of PAX8 during nephric duct differentiation. d) Immunocytochemistry for PAX8 at FTE organoid culture day, day 30 and human fallopian tube tissue. e) Gene expression of PAX8 at organoids culture day 45, human fallopian tube and kidney. The color matrix of the heat map represents the log 2(Ratio) of PAX8 to its expression at the iPSC stage. Relative gene expression to iPSC stage (day 0) was calculated using DDCt method and normalized to endogenous GAPDH level for 87iCTR-n3 iPSC line.
Figure 11:
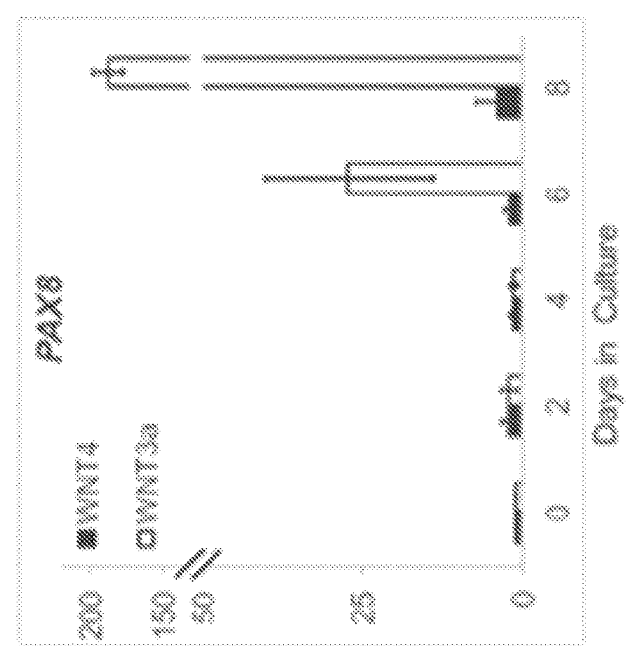

Since Müllerian duct development occurs in parallel to nephric duct, the kinetics of kidney progenitor formation using the Inventors' new differentiation protocol were also characterized. Treating cultures with WNT3A led to increased expression of the renal marker SIX2 and FOXD1, suggesting the formation of the nephric duct and uteric bud and recapitulating published protocols (FIG. 2d, grey bars). Importantly, this protocol was specific to Müllerian duct differentiation, demonstrated by the lack of expression of the early kidney markers SIX2, FOXD1, and PAX8 (FIG. 2d, FIG. 11a black bars and FIG. 11b red channel). In contrast, WNT3A treatment did not yield differentiated Müllerian duct, based on the nearly 10-fold decreased levels of WT1 and OVGP1 compared to WNT4 treatment in FIG. 2b (FIG. 2e). Collectively these results demonstrate that activation of WNT4 followed by Follistatin can selectively differentiate IM into FTE precursor cells.

EXAMPLE 12

Generation and Progressive Maturation of Fallopian Tube Organoid Over Time

Figure 3:
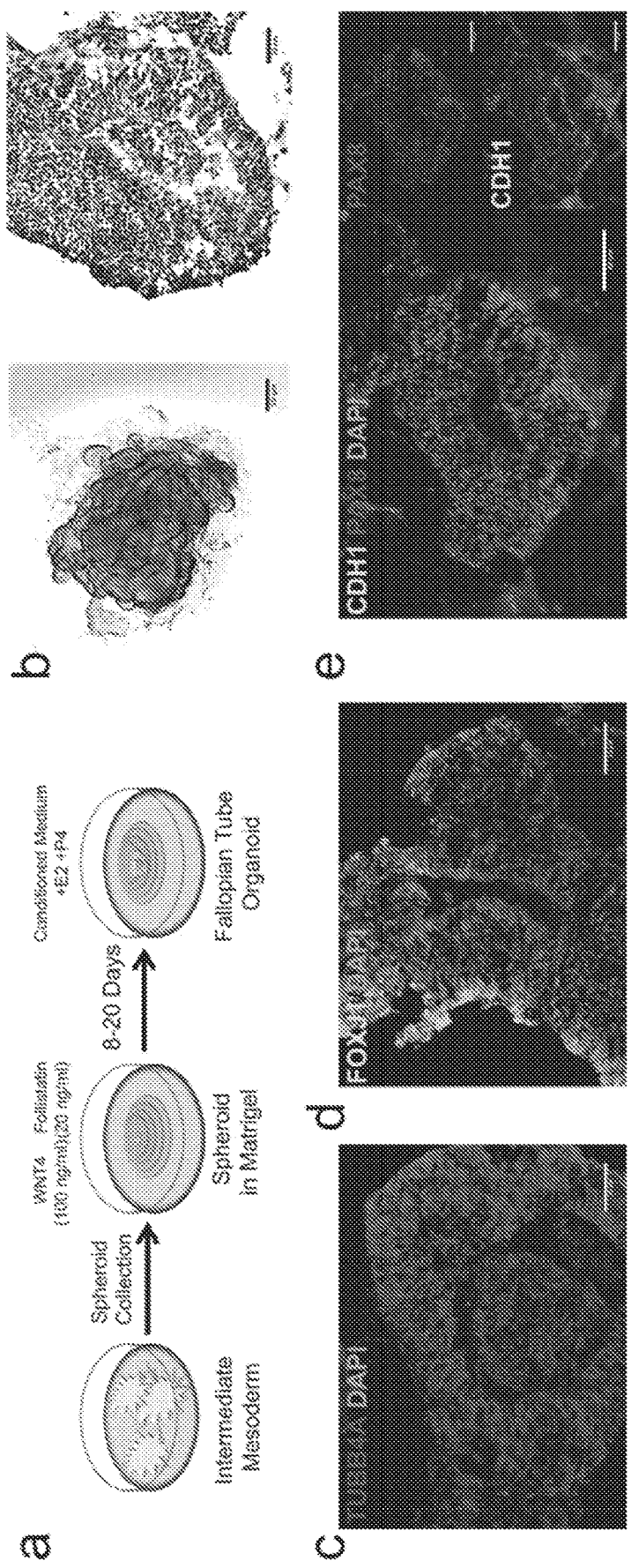
FIG. 3: Progressive Maturation of Fallopian Tube Organoid Over Time in Culture. a) Schematic of factors involved in the differentiation of fallopian tube organoids. b) Bright field image and H&E staining of FTE organoid at day 14. c-e) Immunocytochemistry for FTE markers TUBB4A, FOXJ1 and PAX8 and epithelial marker CDH1 (E-Cadherin) at organoid culture day 14. f) Immunocytochemistry for FTE markers PAX8, TUBB4A, OVGP1 and epithelial marker CDH1 at FTE organoid culture day 45, along with human fallopian tube tissue. g) Gene expression of fallopian tube markers OVGP1 (for 2 different primers), FOXJ1, and TNFaIP2, as well as kidney markers SALL1 and FOXD1 at organoids culture day 45, human fallopian tube and kidney. The color matrix of the heat map represents the log 2(Ratio) of individual gene relative to its expression in iPSC stage. Relative gene expression to iPSC stage (day 0) was calculated using $\Delta\Delta$Ct method and normalized endogenous GAPDH level for 87iCTR-n3 iPSC line. h) H&E staining of FTE organoid at culture day 45 and human fallopian tube tissue.
Figure 3:
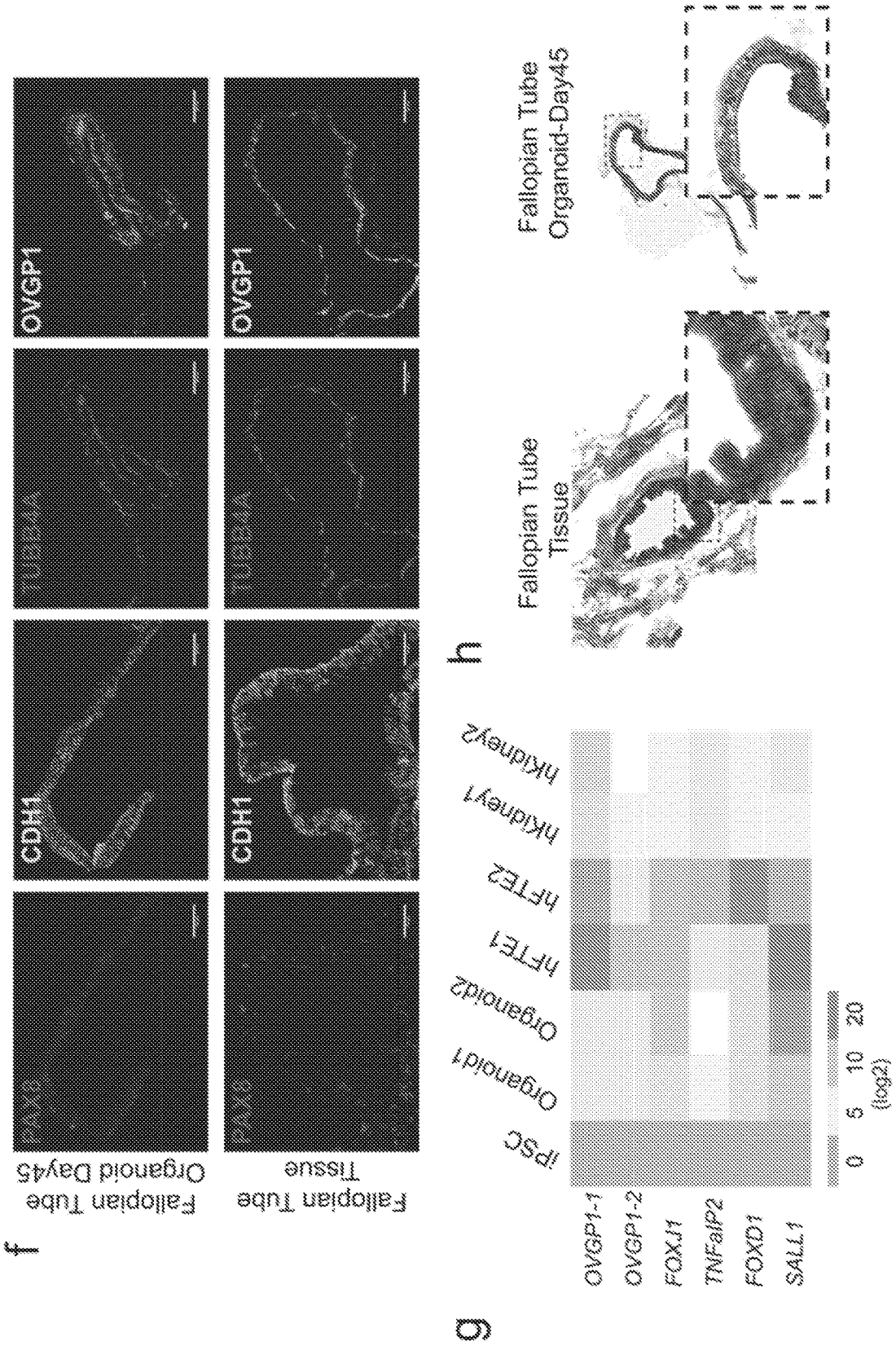
Figure 9:
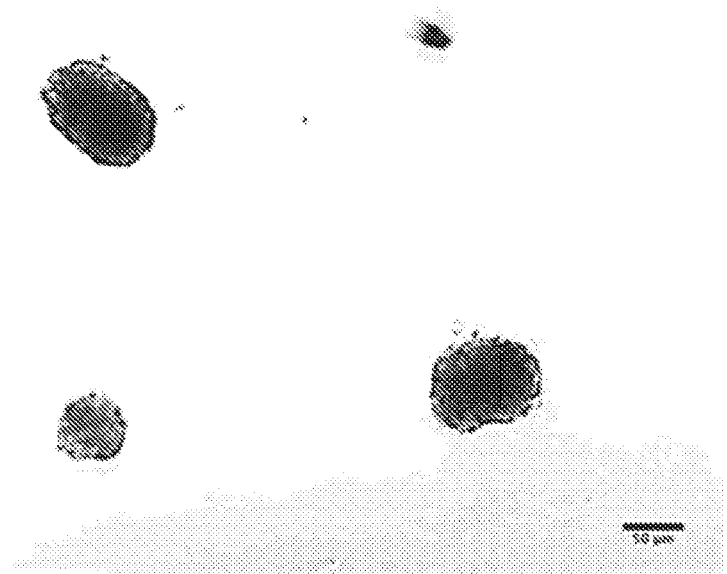
FIG. 9: Bright field image of 3D structure of FTE organoid at day 14 in a) Matrigel with Phenol Red vs b) Matrigel without Phenol Red.
Figure 9:
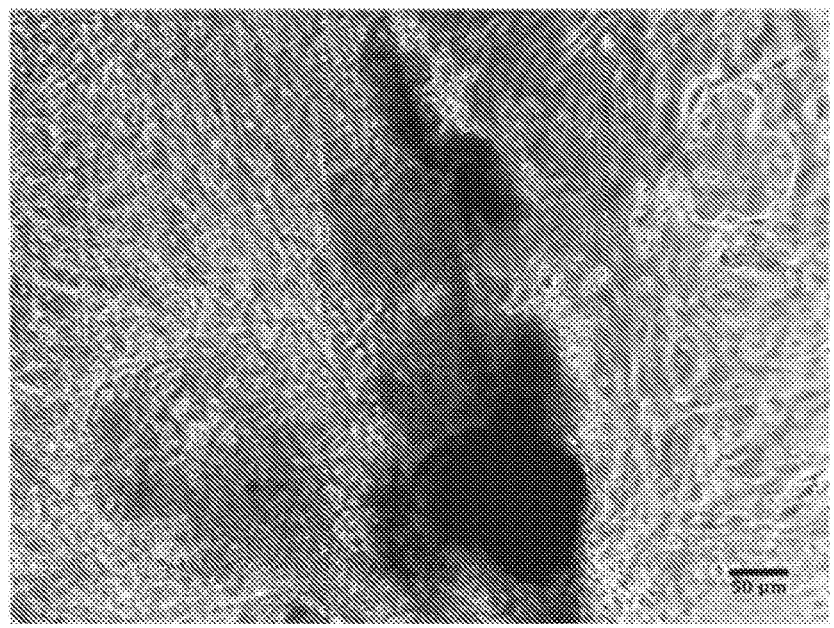
Figure 12:
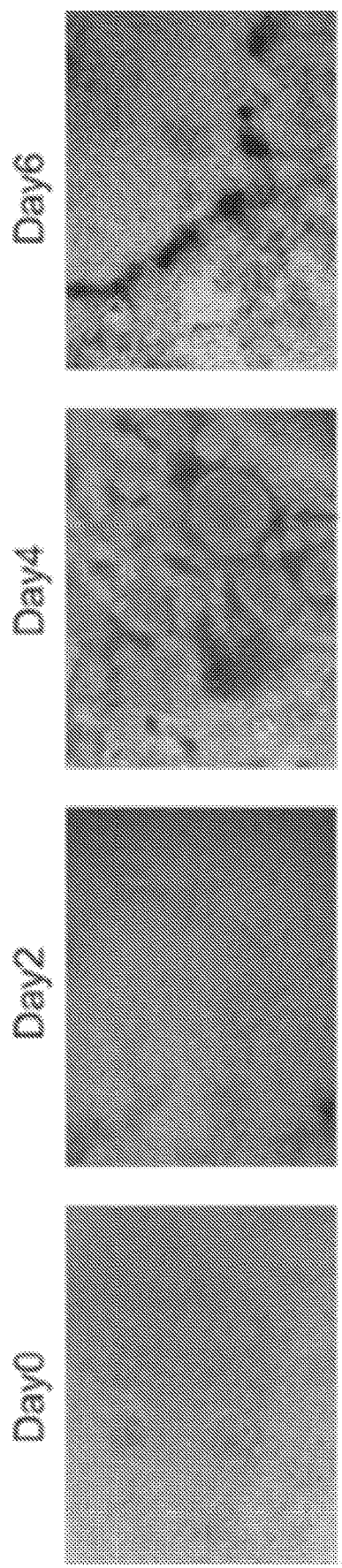
FIG. 12: Bright field image of Müllerian duct differentiation in monolayer culture for 6 days. Red arrow indicates the epithelial bud formation at day 4.

Remarkably, BMP4- and CHIR99021-treated cultures underwent morphogenesis that was similar to embryonic development. Between 3-5 days of treatment, flat cell sheets condensed into epithelial buds (FIG. 12). Once harvested, these buds formed spheroids, which were placed into Matrigel beads along with pro-Müllerian growth factors. Since optimal IM formed at day 4, spheroids were collected on days 3 to 6. Day 4 was ideal for collection of spheroids, as cells collected on day 3 were immature and grew with unstable structure in Matrigel and spherioids collected after day 6 did not persist in culture. When these spheroids were grown in Matrigel that contained phenol red, they formed an organoid structure (FIG. 9a). In contrast, when spheroids were grown in Matrigel not containing phenol red, they became branched and formed an unorganized matrix (FIG. 9b). As phenol red is a weak estrogen mimic, these results indicate the significance of estrogen on FTE differentiation and maturation While the estrogenic properties of phenol-red initially improved organoid growth and organization, it was unable to sustain the organoids over longer periods. Steroid hormones, and estrogen in particular, are known to regulate development of the female reproductive tract, and estrogen has been shown to mediate cellular proliferation and differentiation during embryogenesis[2]. Therefore, to increase the architectural complexity and gain the structure of the plicae, fallopian tube organoids were exposed to estrogen (E2) and progesterone (P4) (FIG. 3a). In addition, conditioned media from FTE cells freshly isolated from patient tissue was used to provide other factors in the fallopian tube milieu that may be necessary for fallopian tube development.

Figure 10:
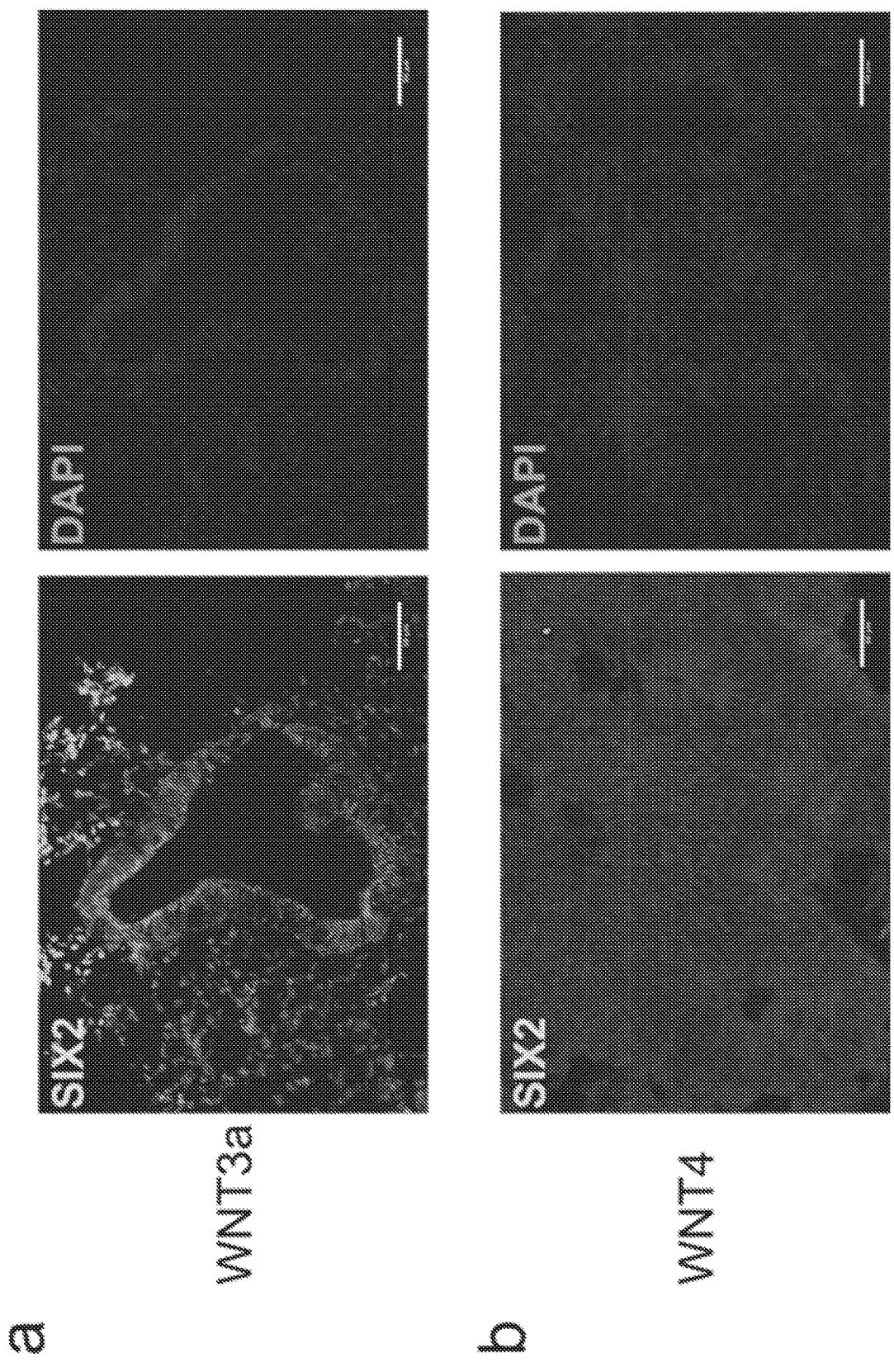
FIG. 10: Immunocytochemistry analysis of day 21 organoid for kidney marker SIX2 with a) WNT3A treatment as a positive control for kidney differentiation compared with b) WNT4 treatment for Müllerian duct differentiation.

This optimized protocol provided long-term organoids in matrigel that displayed luminal structures (FIG. 3a,b). Immunocytochemistry demonstrated that these fallopian tube structures contained ciliated (TUBB4A and FOXJ1) and secretory (PAX8) cellular components (FIG. 3c-e). However, these markers were found throughout the organoid, instead of in specific fallopian tube compartments as would be expected in mature FTE. In addition, there was no expression of the mature epithelial cell marker CHD1 (FIG. 3e). Also, immunocytochemistry confirmed the lack of expression of kidney marker SIX2, compared to WNT3a treatment as a positive control for kidney differentiation (FIG. 10a,b) Collectively, this suggests that while FTE precursor cells were detected in day 14 organoids, functional maturation of FTE required two months, similar to the timeline for human development.

Figure 13:
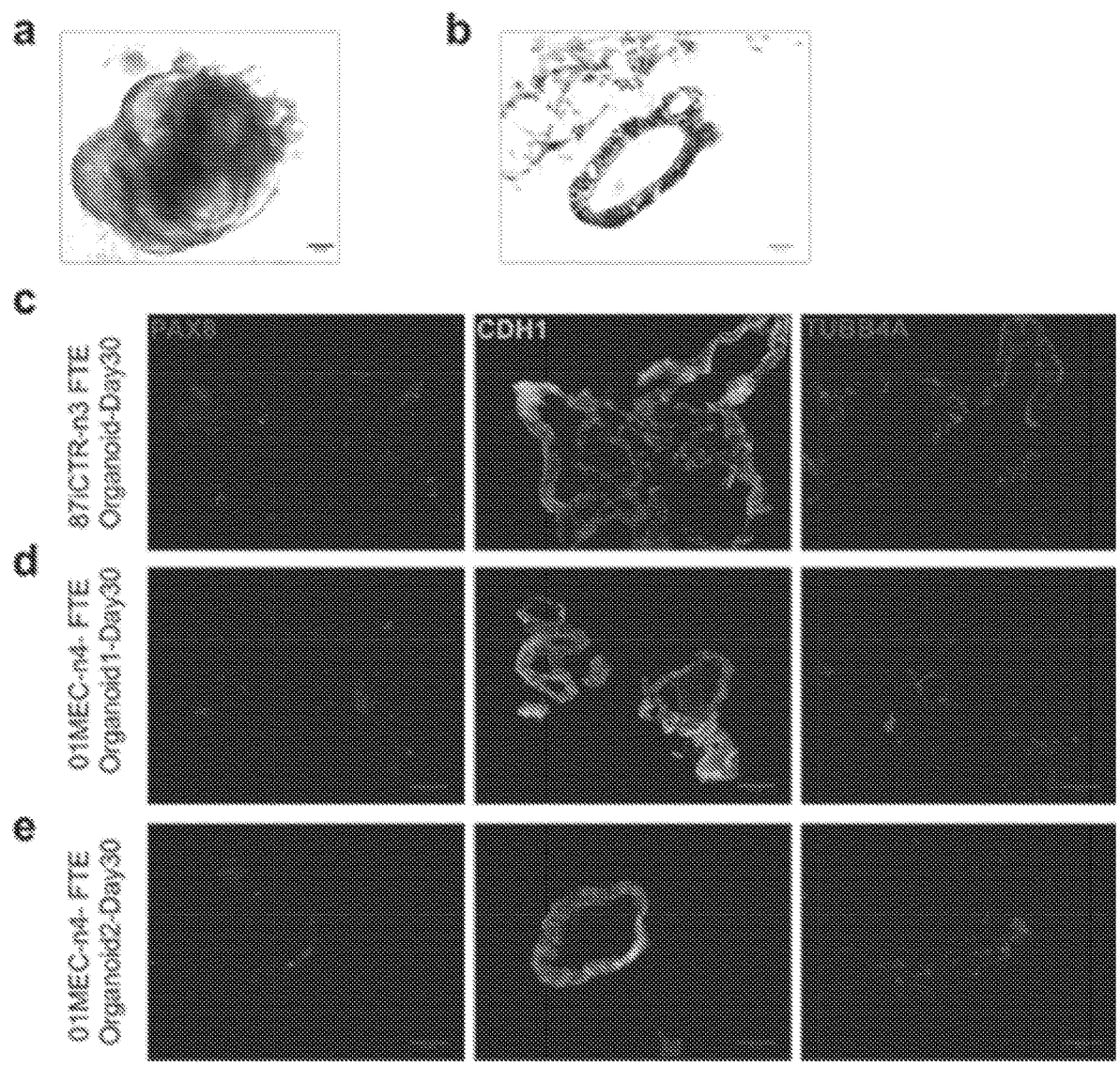
FIG. 13: a) Bright field image of 3D structure of FTE organoid from 01iMEC-n4 iPSC lines at day 30 in. b) H&E staining of FTE organoid from 01iMEC-n4 iPSC lines at day 30. (c-e) Immunocytochemistry for FTE markers TUBB4A and PAX8, and epithelial marker CDH1 (E-Cadherin) at organoid culture day 30, 87CTR-n3 iPSC, 01iMEC-n4 iPSC biological replicate1 and 01iMEC-n4 iPSC biological replicate2 respectively
Figure 14:
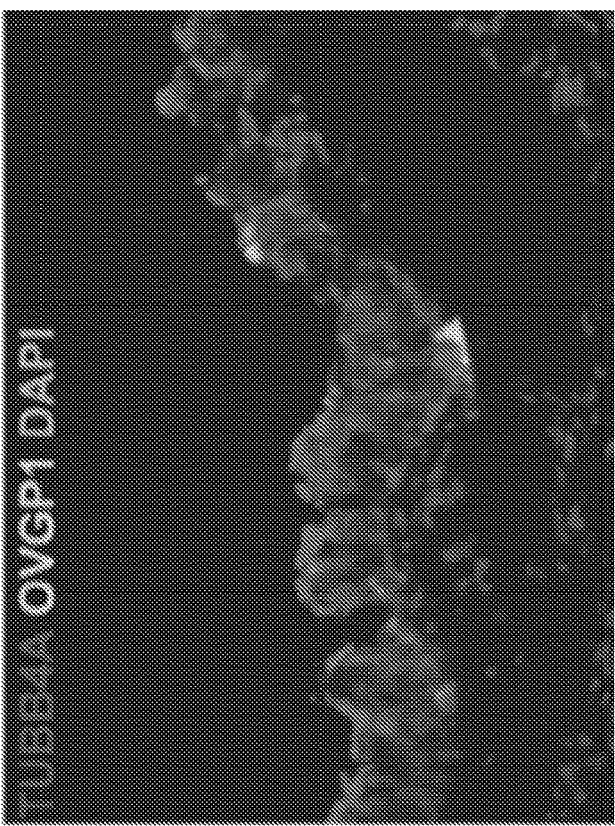
FIG. 14: Development and Characterization of an iPSC-Derived Fallopian Tube Organoid. Immunocytochemistry for FTE markers TUBB4A and OVGP1 at FTE organoid culture day 45, along with human fallopian tube tissue in high magnification.
Figure 14:
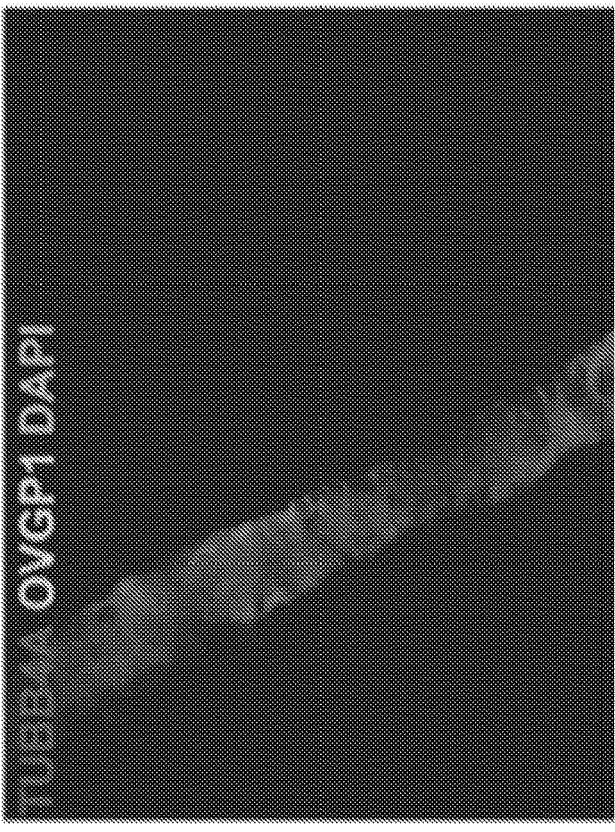

To obtain functional maturation of FTE, the iPSC-derived FTE organoids were extended in culture in 3D Matrigel for an extended period with estrogen and progesterone supplemented media. Immunocytochemistry at day 30 showed that secretory cell marker PAX8 and ciliated cell marker TUBB4A, as well as the epithelial cell marker CDH1, exhibited similar expression patterns in FTE organoids model from two different iPSC lines (FIG. 13), Results at 45 days showed that the FTE cil ated marker, TUBB4A, and secretory cell markers, OVGP1 and PAX8 and the epithelial cell marker, CDH1, were now expressed in the expected sub-compartments seen in mature FTE, with TUBB4A being highly expressed along the lumen (FIG. 3f, FIG. 14). Importantly, the cellular expression and organization was comparable to fresh human fallopian tube tissue (FIG. 3f). The differentiation of iPSC-derived organoids into fallopian tube mature cells overtime was further demonstrated heat map analysis, which showed increased expression of fallopian tube-specific ciliated markers, FOXJ1 and secretory cell markers, OVGP1 that were similar to human fallopian tube tissue (FIG. 3g). Critically, iPSC-derived FTE organoids not only expressed both ciliated and secretory cell markers but also they formed visible cilia, further demonstrating that this novel model closely mimics the proper physiology and anatomy of the human FTE (FIG. 3h).

EXAMPLE 13

Discussion

Human iPSCs are derived using technologies to reprogram adult cells back to a pluripotent state with the subsequent potential to differentiated into any cell type. Reprogramming to human iPSC possesses the essential advantages of eliminating the requirement for embryonic material while allowing for the generation of pluripotent cells with known genetic factor in a patient-specific manner. Moreover, combined with 3D cell culture techniques, 3D-iPSC derived organoid models can be developed which reconstitute features of organs, thereby overcoming many of the limitations of traditional monolayer cell culture systems by mimicking more closely the complex cellular heterogeneity and cell-cell/cell-matrix interactions.

Intermediate mesoderm generates several components of the urogenital system, including reproductive tracts and also the kidneys, the gonads, and their respective duct systems. Priming the IM into only the desired cell fate has been a challenge for the iPSC-derived organoid model. To the Inventors' knowledge, all established iPSC-derived IM platforms have been developed to model the kidney formation using the combination of WNT, Nodal/Activin, and BMP signaling pathways. In this study, different WNT signaling pathways were modulated to successfully develop a novel differentiation protocol with key components to drive Müllerian duct and the female reproductive tract development rather than kidney. The most efficient differentiation platform to mimic embryonic fallopian tube development used CHIR99021 and activin A, along with BMP4 that was discovered to be critical for conversion of IM into female reproductive tract or Müllerian duct. To the Inventors' knowledge, this study presents the first iPSC-derived FTE in vitro model. The Inventors have demonstrated direct differentiation of human iPSCs into a fallopian tube-like precursor cells and, moreover, established iPSC-derived human fallopian tube organoids that recapitulate complexity of 3D architecture of FTE tissue.

During embryogenesis, WNT signaling pathways play a prominent role in regulating cell fate specification and in determining cell polarity and migration. WNT signaling is often correlated with cell proliferation and tissue repair after acute injury, rather than with differentiation of stem cells into adult tissues. However, recent human FTE organoid models with bi-potent FTE stem cells indicated the function of WNT3A in fallopian epithelial renewal and the regulation of stemness, suggesting the distinct role of WNT pathways in embryonic development and adult stem cell function. The current study found that activation of WNT4, instead of WNT3A, and activation of the downstream effector Follistatin were vital to specify IM differentiation into Müllerian duct and an FTE cell fate in vitro. Interestingly, the Inventors also showed that subsequent activation of WNT3A rather than WNT4 promoted nephric duct formation, which reflects the different molecular ability of WNTs to regulate specific cell fates.

Many fundamental cellular processes are differentially regulated between 2D and 3D cultures. Exposure of differentiated iPSCs to a 3D growth platform enabled them to self-organize into luminal structures that model fallopian tube function with secretory and ciliated cell components. Critically, the exposure to primary fallopian tube epithelial conditioned media is required for maintenance of 3D FTE luminal structure and architecture, indicating that there are unknown factors responsible for the organization of cellular structure of the fallopian tube.

In this study, the Inventors generated the basis platform for direct differentiation of iPSC into fallopian tube epithelial cell, however there is room for further improvement with regard to long term culturing and functional maturity. The growth and successful cultivation may dependent on different cell-matrix interactions and some other growth factors, which needs to further address.

Induced PSC-based in vitro models of cancer can help to understand pathological processes at the molecular and cellular level. In addition, they provide a critical platform to study drug resistance and to develop novel drug therapies. Importantly for ovarian cancer, iPSC-derived fallopian tube organoids can provide a faithful human cellular model to investigate the fallopian tube origin of serous carcinogenesis in ovarian cancer and to explore early cancer pathogenesis and progression. This platform can also be used study germline mutations that effect ovarian cancer development and to identify the critical steps and the order of genetic alterations involved with high grade serous carcinogenesis. In summary, iPSC-derived fallopian tube epithelium provides a powerful in vitro model of ovarian cancer that can be used to recapitulate early de novo genomic alterations, faithfully model disease progression and ultimately uncover novel treatments.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are fallopian tube epithelium, cells, organoids, and tissue products thereof, methods of generating fallopian tube epithelium, prognostic and/or diagnostic panels that include nucleic acid, peptide and proteins sequences associated with cancers such as ovarian cancer, and the techniques associated with the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law.

Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method for generating a fallopian tube epithelium (FTE), the method comprising:
   providing a quantity of human pluripotent stem cells (hPSCs);
   culturing the hPSCs in the presence of at least one first growth factor comprising Activin A and at least one first induction molecule comprising CHIR99021 to generate mesoderm cells;
   further culturing the mesoderm cells in the presence of at least one second growth factor comprising BMP4, at least one second induction molecule comprising CHIR99021, and at least one first kinase inhibitor comprising ROCK inhibitor Y-27632 to generate intermediate mesoderm (IM) cells;
   additionally culturing the IM cells in the presence of at least one third growth factor comprising WNT4, and at least one second kinase inhibitor comprising ROCK inhibitor Y-27632 to generate Mullerian epithelium cells; and
   differentiating the Mullerian epithelium cells by addition of one or more fourth growth factors selected from follistatin, estrogen, or progesterone into FTE.

2. The method of claim 1, wherein the hPSCs are human induced pluripotent stem cells (hiPSCs).

3. The method of claim 1, wherein culturing the hPSCs comprises about 2 days.

4. The method of claim 1, wherein further culturing the mesoderm cells comprises about 2 days.

5. The method of claim 1, wherein additionally culturing the IM cells comprises about 2 days.

6. The method of claim 1, wherein the one or more fourth growth factors comprise follistatin, estrogen, and progesterone.

7. The method of claim 1, wherein the IM cells are organized as spheroids.

8. The method of claim 7, wherein the spheroids are subsequently cultured in a matrix.

9. The method of claim 1, wherein the FTE are organized as organoids.

10. The method of claim 9, wherein the FTE organoids are matured by further culturing for about 14-65 days.

11. The method of claim 1, wherein the mesoderm cells express one or more of: BRACHYURY or MIXL1.

12. The method of claim 1, wherein the IM cells express one or more of: PAX2, OSR1, GATA3, or WT1.

13. The method of claim 1, wherein the Mullerian epithelium cells express one or more of: WT1 or OVGP1.

14. The method of claim 1, wherein the Mullerian epithelium cells do not express one or more of: SIX2, FOXD1, CDX2 or NKX2-1.

15. A method of generating fallopian tube epithelium (FTE) organoids, the method comprising:
    providing a quantity of intermediate mesoderm (IM) cells;
    culturing the IM cells in a matrix and in the presence of at least one first growth factor comprising WNT4, and at least one kinase inhibitor comprising ROCK inhibitor Y-27632 to generate Mullerian epithelium cells; and
    differentiating the Mullerian epithelium cells by addition of one or more second growth factors selected from follistatin, estrogen, or progesterone into FTE organoids.

16. The method of claim 15, wherein culturing the IM cells comprises about 2 days.

17. The method of claim 15, wherein the one or more second growth factors comprise follistatin, estrogen, and progesterone.

18. The method of claim 15, wherein the FTE organoids are matured by further culturing for about 14-65 days.

19. The method of claim 15, wherein the FTE organoids express one or more of: TUBB4A, FOXJ1, or PAX8.

* * * * *

```
                              SEQUENCE LISTING

<160> NUMBER OF SEQ ID NOS: 42

<210> SEQ ID NO 1
<211> LENGTH: 20
<212> TYPE: DNA
<213> ORGANISM: Artificial Sequence
<220> FEATURE:
<223> OTHER INFORMATION: BRACHYURY - Forward

<400> SEQUENCE: 1
gctgtgacag gtacccaacc                                                  20

<210> SEQ ID NO 2
<211> LENGTH: 21
<212> TYPE: DNA
<213> ORGANISM: Artificial Sequence
<220> FEATURE:
<223> OTHER INFORMATION: BRACHYURY - Reverse

<400> SEQUENCE: 2
catgcaggtg agttgtcaga a                                                21

<210> SEQ ID NO 3
<211> LENGTH: 20
<212> TYPE: DNA
<213> ORGANISM: Artificial Sequence
<220> FEATURE:
<223> OTHER INFORMATION: FOXD1 - Forward

<400> SEQUENCE: 3
gactctgcac caagggactg                                                  20

<210> SEQ ID NO 4
<211> LENGTH: 25
<212> TYPE: DNA
<213> ORGANISM: Artificial Sequence
<220> FEATURE:
<223> OTHER INFORMATION: FOXD1 - Reverse

<400> SEQUENCE: 4
caattggaaa tcctagcagt aaagt                                            25

<210> SEQ ID NO 5
<211> LENGTH: 18
<212> TYPE: DNA
<213> ORGANISM: Artificial Sequence
<220> FEATURE:
```

```
<223> OTHER INFORMATION: FOXJ1 - Forward

<400> SEQUENCE: 5
ggggtgggag caacttct                                                 18

<210> SEQ ID NO 6
<211> LENGTH: 23
<212> TYPE: DNA
<213> ORGANISM: Artificial Sequence
<220> FEATURE:
<223> OTHER INFORMATION: FOXJ1 - Reverse

<400> SEQUENCE: 6
cctcctccga ataagtatgt ggt                                           23

<210> SEQ ID NO 7
<211> LENGTH: 20
<212> TYPE: DNA
<213> ORGANISM: Artificial Sequence
<220> FEATURE:
<223> OTHER INFORMATION: GAPDH - Forward

<400> SEQUENCE: 7
gtggacctga cctgccgtct                                               20

<210> SEQ ID NO 8
<211> LENGTH: 20
<212> TYPE: DNA
<213> ORGANISM: Artificial Sequence
<220> FEATURE:
<223> OTHER INFORMATION: GAPDH - Reverse

<400> SEQUENCE: 8
ggaggagtgg gtgtcgctgt                                               20

<210> SEQ ID NO 9
<211> LENGTH: 20
<212> TYPE: DNA
<213> ORGANISM: Artificial Sequence
<220> FEATURE:
<223> OTHER INFORMATION: GATA3 - Forward

<400> SEQUENCE: 9
ctcattaagc ccaagcgaag                                               20

<210> SEQ ID NO 10
<211> LENGTH: 20
<212> TYPE: DNA
<213> ORGANISM: Artificial Sequence
<220> FEATURE:
<223> OTHER INFORMATION: GATA3 - Reverse

<400> SEQUENCE: 10
gtctgacagt tcgcacagga                                               20

<210> SEQ ID NO 11
<211> LENGTH: 22
<212> TYPE: DNA
<213> ORGANISM: Artificial Sequence
<220> FEATURE:
<223> OTHER INFORMATION: HOXB7 - Forward

<400> SEQUENCE: 11
ccgagagtaa cttccggatc ta                                            22
```

```
<210> SEQ ID NO 12
<211> LENGTH: 22
<212> TYPE: DNA
<213> ORGANISM: Artificial Sequence
<220> FEATURE:
<223> OTHER INFORMATION: HOXB7 - Reverse

<400> SEQUENCE: 12
cgtcaggtag cgattgtagt ga                                              22

<210> SEQ ID NO 13
<211> LENGTH: 19
<212> TYPE: DNA
<213> ORGANISM: Artificial Sequence
<220> FEATURE:
<223> OTHER INFORMATION: MIXL1 - Forward

<400> SEQUENCE: 13
ggtaccccga catccactt                                                  19

<210> SEQ ID NO 14
<211> LENGTH: 21
<212> TYPE: DNA
<213> ORGANISM: Artificial Sequence
<220> FEATURE:
<223> OTHER INFORMATION: MIXL1 - Reverse

<400> SEQUENCE: 14
gcctgttctg gaaccatacc t                                               21

<210> SEQ ID NO 15
<211> LENGTH: 20
<212> TYPE: DNA
<213> ORGANISM: Artificial Sequence
<220> FEATURE:
<223> OTHER INFORMATION: NCAM - Forward

<400> SEQUENCE: 15
gattcctcct ccaccctcac                                                 20

<210> SEQ ID NO 16
<211> LENGTH: 20
<212> TYPE: DNA
<213> ORGANISM: Artificial Sequence
<220> FEATURE:
<223> OTHER INFORMATION: NCAM - Reverse

<400> SEQUENCE: 16
caatattctg cctggcctgg                                                 20

<210> SEQ ID NO 17
<211> LENGTH: 18
<212> TYPE: DNA
<213> ORGANISM: Artificial Sequence
<220> FEATURE:
<223> OTHER INFORMATION: NKX2.1 - Forward

<400> SEQUENCE: 17
tcatttgttg gcgactgg                                                   18

<210> SEQ ID NO 18
<211> LENGTH: 20
<212> TYPE: DNA
<213> ORGANISM: Artificial Sequence
<220> FEATURE:
<223> OTHER INFORMATION: NKX2.1 - Reverse
```

```
<400> SEQUENCE: 18
tgctttggac tcatcgacat                                           20

<210> SEQ ID NO 19
<211> LENGTH: 18
<212> TYPE: DNA
<213> ORGANISM: Artificial Sequence
<220> FEATURE:
<223> OTHER INFORMATION: OSR1 - Forward

<400> SEQUENCE: 19
ggacctctgc ggaacaag                                             18

<210> SEQ ID NO 20
<211> LENGTH: 18
<212> TYPE: DNA
<213> ORGANISM: Artificial Sequence
<220> FEATURE:
<223> OTHER INFORMATION: OSR1 - Reverse

<400> SEQUENCE: 20
tgcagggaag ggtggata                                             18

<210> SEQ ID NO 21
<211> LENGTH: 19
<212> TYPE: DNA
<213> ORGANISM: Artificial Sequence
<220> FEATURE:
<223> OTHER INFORMATION: OVGP1 - Forward

<400> SEQUENCE: 21
aagctgttgc tgtgggttg                                            19

<210> SEQ ID NO 22
<211> LENGTH: 19
<212> TYPE: DNA
<213> ORGANISM: Artificial Sequence
<220> FEATURE:
<223> OTHER INFORMATION: OVGP1 - Reverse

<400> SEQUENCE: 22
tgtgcccagt tggtgaaat                                            19

<210> SEQ ID NO 23
<211> LENGTH: 25
<212> TYPE: DNA
<213> ORGANISM: Artificial Sequence
<220> FEATURE:
<223> OTHER INFORMATION: OVGP1-2 - Forward

<400> SEQUENCE: 23
aattctctac ccagagttca acaaa                                     25

<210> SEQ ID NO 24
<211> LENGTH: 22
<212> TYPE: DNA
<213> ORGANISM: Artificial Sequence
<220> FEATURE:
<223> OTHER INFORMATION: OVGP1-2 - Reverse

<400> SEQUENCE: 24
ccgatggaca gtagtgtttt ca                                        22

<210> SEQ ID NO 25
<211> LENGTH: 18
```

```
<212> TYPE: DNA
<213> ORGANISM: Artificial Sequence
<220> FEATURE:
<223> OTHER INFORMATION: PAX2 - Forward

<400> SEQUENCE: 25
gaagtgcccc cttgtgtg                                                 18

<210> SEQ ID NO 26
<211> LENGTH: 20
<212> TYPE: DNA
<213> ORGANISM: Artificial Sequence
<220> FEATURE:
<223> OTHER INFORMATION: PAX2 - Reverse

<400> SEQUENCE: 26
tcgttgtagg ccgtgtactg                                               20

<210> SEQ ID NO 27
<211> LENGTH: 20
<212> TYPE: DNA
<213> ORGANISM: Artificial Sequence
<220> FEATURE:
<223> OTHER INFORMATION: POU5F1 - Forward

<400> SEQUENCE: 27
acccacactg cagcagatca                                               20

<210> SEQ ID NO 28
<211> LENGTH: 19
<212> TYPE: DNA
<213> ORGANISM: Artificial Sequence
<220> FEATURE:
<223> OTHER INFORMATION: POU5F1 - Reverse

<400> SEQUENCE: 28
ccacactcgg accacatcc                                                19

<210> SEQ ID NO 29
<211> LENGTH: 20
<212> TYPE: DNA
<213> ORGANISM: Artificial Sequence
<220> FEATURE:
<223> OTHER INFORMATION: SALL1 - Forward

<400> SEQUENCE: 29
attgcagcct agccaaaaag                                               20

<210> SEQ ID NO 30
<211> LENGTH: 20
<212> TYPE: DNA
<213> ORGANISM: Artificial Sequence
<220> FEATURE:
<223> OTHER INFORMATION: SALL1 - Reverse

<400> SEQUENCE: 30
accagctgag cagaaaggtc                                               20

<210> SEQ ID NO 31
<211> LENGTH: 20
<212> TYPE: DNA
<213> ORGANISM: Artificial Sequence
<220> FEATURE:
<223> OTHER INFORMATION: SIX2 - Forward

<400> SEQUENCE: 31
```
caggtcagca actggttcaa                                                    20

<210> SEQ ID NO 32
<211> LENGTH: 20
<212> TYPE: DNA
<213> ORGANISM: Artificial Sequence
<220> FEATURE:
<223> OTHER INFORMATION: SIX2 - Reverse

<400> SEQUENCE: 32
agctgcctaa caccgacttg                                                    20

<210> SEQ ID NO 33
<211> LENGTH: 18
<212> TYPE: DNA
<213> ORGANISM: Artificial Sequence
<220> FEATURE:
<223> OTHER INFORMATION: SOX17 - Forward

<400> SEQUENCE: 33
acgccgagtt gagcaaga                                                      18

<210> SEQ ID NO 34
<211> LENGTH: 18
<212> TYPE: DNA
<213> ORGANISM: Artificial Sequence
<220> FEATURE:
<223> OTHER INFORMATION: SOX17 - Reverse

<400> SEQUENCE: 34
tctgcctcct ccacgaag                                                      18

<210> SEQ ID NO 35
<211> LENGTH: 21
<212> TYPE: DNA
<213> ORGANISM: Artificial Sequence
<220> FEATURE:
<223> OTHER INFORMATION: SOX2 - Forward

<400> SEQUENCE: 35
gggggaatgg accttgtata g                                                  21

<210> SEQ ID NO 36
<211> LENGTH: 20
<212> TYPE: DNA
<213> ORGANISM: Artificial Sequence
<220> FEATURE:
<223> OTHER INFORMATION: SOX2 - Reverse

<400> SEQUENCE: 36
gcaaagctcc taccgtacca                                                    20

<210> SEQ ID NO 37
<211> LENGTH: 22
<212> TYPE: DNA
<213> ORGANISM: Artificial Sequence
<220> FEATURE:
<223> OTHER INFORMATION: TDGF1 - Forward

<400> SEQUENCE: 37
agggaacaat gacagagtgt ga                                                 22

<210> SEQ ID NO 38
<211> LENGTH: 20
<212> TYPE: DNA
<213> ORGANISM: Artificial Sequence

```
<220> FEATURE:
<223> OTHER INFORMATION: TDGF1 - Reverse

<400> SEQUENCE: 38
cccgagatgg acgagcaaat                                                 20

<210> SEQ ID NO 39
<211> LENGTH: 18
<212> TYPE: DNA
<213> ORGANISM: Artificial Sequence
<220> FEATURE:
<223> OTHER INFORMATION: TNFaIP2 - Forward

<400> SEQUENCE: 39
gagccacggc tttgacac                                                   18

<210> SEQ ID NO 40
<211> LENGTH: 20
<212> TYPE: DNA
<213> ORGANISM: Artificial Sequence
<220> FEATURE:
<223> OTHER INFORMATION: TNFaIP2 - Reverse

<400> SEQUENCE: 40
gtgcgtgaac ctcttgaaca                                                 20

<210> SEQ ID NO 41
<211> LENGTH: 20
<212> TYPE: DNA
<213> ORGANISM: Artificial Sequence
<220> FEATURE:
<223> OTHER INFORMATION: WT1 - Forward

<400> SEQUENCE: 41
gaatgcatga cctggaatca                                                 20

<210> SEQ ID NO 42
<211> LENGTH: 20
<212> TYPE: DNA
<213> ORGANISM: Artificial Sequence
<220> FEATURE:
<223> OTHER INFORMATION: WT1 - Reverse

<400> SEQUENCE: 42
tctgcccttc tgtccatttc                                                 20
```